(12) United States Patent
Christian et al.

(10) Patent No.: US 7,728,971 B2
(45) Date of Patent: *Jun. 1, 2010

(54) METHOD AND APPARATUS FOR PERFORMING SPECTROSCOPY DOWNHOLE WITHIN A WELLBORE

(75) Inventors: Sean M. Christian, Land O'Lakes, FL (US); Jess V. Ford, Arnold, MO (US); Mike Ponstingl, Saint Louis, MO (US); Anthony Johnson, Saint Louis, MO (US); Sven Kruger, Berlin-Adlershof (DE); Margaret C. Waid, Medicine Park, OK (US); Bryan Kasperski, Azle, TX (US); Enrique Prati, Houston, TX (US)

(73) Assignee: Precision Energy Services, Inc., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/342,650

(22) Filed: Dec. 23, 2008

(65) Prior Publication Data
US 2009/0103087 A1   Apr. 23, 2009

Related U.S. Application Data

(63) Continuation of application No. 11/865,587, filed on Oct. 1, 2007, now Pat. No. 7,508,506, which is a continuation of application No. 11/696,005, filed on Apr. 3, 2007, now Pat. No. 7,440,098.

(60) Provisional application No. 60/827,837, filed on Oct. 2, 2006, provisional application No. 60/827,837, filed on Oct. 2, 2006, provisional application No. 60/744,246, filed on Apr. 4, 2006.

(51) Int. Cl.
*G01J 3/08* (2006.01)
*G01J 3/42* (2006.01)

(52) U.S. Cl. ............... 356/319; 250/269.1; 356/325; 356/328

(58) Field of Classification Search ............... 356/310, 356/319, 325, 326, 328, 330
See application file for complete search history.

(56) References Cited

U.S. PATENT DOCUMENTS 5,128,797 A   7/1992 Sachse et al.

(Continued)

OTHER PUBLICATIONS

International Search Report, International Patent Application No. PCT/US2007/080112, mailed on Mar. 25, 2008, 6 pages.

(Continued)

*Primary Examiner*—F. L Evans
(74) *Attorney, Agent, or Firm*—Lewis, Rice & Fingersh, L.C.

(57) ABSTRACT

An analysis system, tool, and method for performing downhole fluid analysis, such as within a wellbore. The analysis system, tool, and method provide for a tool including a spectroscope for use in downhole fluid analysis which utilizes an adaptive optical element such as a Micro Mirror Array (MMA) and two distinct light channels and detectors to provide real-time scaling or normalization.

24 Claims, 14 Drawing Sheets

U.S. PATENT DOCUMENTS

| | | | |
|---|---|---|---|
| 5,337,621 | A | 8/1994 | Spease |
| 5,440,118 | A | 8/1995 | Roscoe |
| 5,504,575 | A | 4/1996 | Stafford |
| 5,629,125 | A | 5/1997 | Leblans et al. |
| 5,828,066 | A | 10/1998 | Messerschmidt |
| 6,128,078 | A | 10/2000 | Fateley |
| 6,504,943 | B1 | 1/2003 | Sweatt et al. |
| 6,571,118 | B1 | 5/2003 | Utzinger et al. |
| 6,600,591 | B2 | 7/2003 | Anderson et al. |
| 6,678,050 | B2 | 1/2004 | Pope et al. |
| 6,753,960 | B1 | 6/2004 | Polynkin et al. |
| 6,768,105 | B2 | 7/2004 | Mullins et al. |
| 6,781,691 | B2 | 8/2004 | MacKinnon et al. |
| 7,265,830 | B2 | 9/2007 | Wang |
| 7,440,098 | B2 | 10/2008 | Christian et al. |
| 7,508,506 | B2 * | 3/2009 | Christian et al. ............ 356/319 |
| 2004/0169858 | A1 | 9/2004 | Da Silva |
| 2004/0201850 | A1 | 10/2004 | Hajian et al. |
| 2004/0239923 | A1 | 12/2004 | Adams et al. |
| 2004/0239931 | A1 | 12/2004 | Teichmann et al. |
| 2005/0185179 | A1 | 8/2005 | Wang |
| 2005/0243312 | A1 | 11/2005 | Geshwind et al. |
| 2007/0159625 | A1 | 7/2007 | DiFoggio |
| 2008/0174777 | A1 | 7/2008 | Carron |

OTHER PUBLICATIONS

Dudley, D., et al., "Emerging Digital Micromirror Device (DMD) Applications," DLP Products New Applications, Texas Instruments, Inc., undated, 12 pages.

Wagner, E. P. II, et al., "Construction and Evaluation of a Visible Spectrometer Using Digital Micromirror Spatial Light Modulation," Applied Spectroscopy, 1995, pp. 1715-1719, vol. 49, No. 11.

Ford, J. E., et al., "Dynamic Spectral Power Equalization Using Micro-Opto-Mechanics," IEEE Photonics Technology Letters, Oct. 1998, pp. 1440-1442, vol. 10, No. 10.

Duncan, W. M., "Dynamic Optical Filtering in DWDM Systems Using the DMD," Solid State Electronics, 2002, pp. 1583-1585, vol. 46.

Lerner, J.M., et al., "The Optics of Spectroscopy—A Tutorial," Instruments SA, Inc., 1988, 61 pages.

Spudich, T. M., et al., "Potential for using a Digital Micromirror Device as a Signal Multiplexer in Visible Spectrscopy," Applied Spectroscopy, 2003, pp. 733-736, vol. 57, No. 7.

Deverse, R. A., et al, "Realization of the Hadamard Multiplex Advantage Using a Programmable Optical Mask in a Dispersive Flat-Field Near-Infrared Spectrometer," Applied Spectroscopy, 2000, pp. 1751-1758, vol. 54, No. 12.

Badry, R., et al., "Downhole Optical Analysis of Formation Fluids," Oilfield Review, Jan. 1994, pp. 21-28.

Schroeder, R., "Slick Engineering," Spie's OE Magazine, May 2003, pp. 18-20.

Raghuraman, B., "Real-Time Downhold pH Measurement Using Optical Spectroscopy," SPE 93057, Society of Petroleum Engineers, 2005, pp. 1-11.

Sirkis, J., "Multifunctionality the Key in Challenging Instrumentation Markets," Lightwave Magazine, Mar. 2003, 5 pages.

Meyer, R., "Ritmos: A Micromirror—Based Multi-Object Spectrometer," Proceedings of the SPIE, 2004, pp. 1-20.

Smits, A. R., "In-Situ Optical Fluid Analysis as a Aid to Wireline Formation Sampling," SPE Formation Evaluation, Jun. 1995, pp. 91-98.

Texas Instruments, Application Report, "Single Panel DLP Projection System Optics," Mar. 2005, pp. 1-32.

Texas Instruments, Product Preview, "DMD 0.7 XGA 12° LVDS DMD Discovery," Jul. 2005, pp. 1-22.

Texas Instruments, Product Preview Data Sheet, "DMD 0.7 XGA 12° DDR DMD Discovery," Aug. 30, 2005, pp. 1-20.

Texas Instruments, "DMD Discovery 1100 Chip Set," 2004, 2 pages.

Texas Instruments, "DMD Discovery 3000 Digital Controller (DDC3000) Starter Kit Technical Reference Manual," Oct. 2005, 28 pages.

Texas Instruments, "DMD Discovery 1100 Controller Board and Starter Kit," Oct. 2004, 41 pages.

Texas Instruments, "DMD Discovery 1100 Controller Board GUI User's & Programmer's Guide," Sep. 2004, 42 pages.

Baker Hughes, "RCI Reservoir Characterization Instrument," 2000, 16 pages.

Baker Hughes, "SampleView," 2000, 2 pages.

Schlumberger, "Fundamentals of Formation Testing," 2006, pp. 1-5, 27-29, 55-67, 99-124, 199-202, Schlumberger Marketing Communications, Sugar Land, Texas, United States.

* cited by examiner

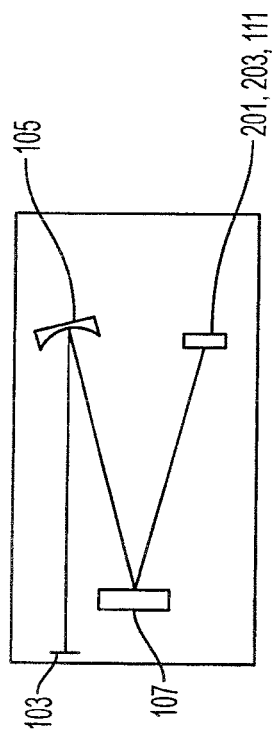
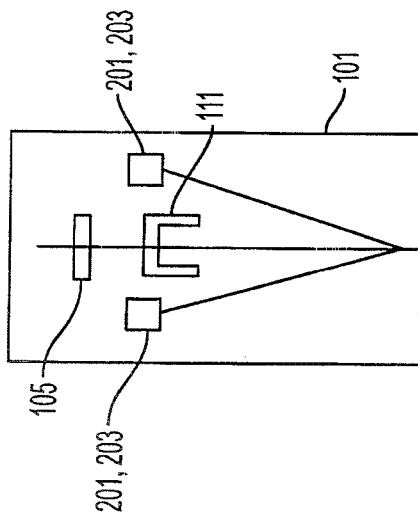
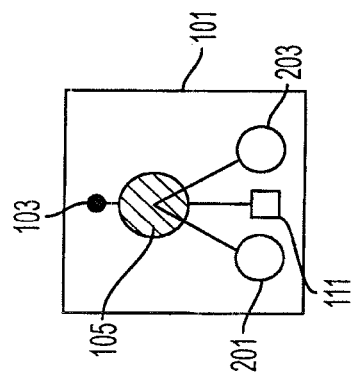
FIG. 9A
FIG. 9B
FIG. 9C

METHOD AND APPARATUS FOR PERFORMING SPECTROSCOPY DOWNHOLE WITHIN A WELLBORE

CROSS REFERENCE TO RELATED APPLICATIONS

This application is a Continuation of U.S. patent application Ser. No. 11/865,587 filed Oct. 1, 2007, now U.S. Pat. No. 7,508,506 which claims benefit of U.S. Provisional Patent Application Ser. No.: 60/827,837 filed Oct. 2, 2006 and is also a Continuation-in-Part (CIP) of U.S. patent application Ser. No. 11/696,005, filed Apr. 3, 2007, now U.S. Pat. No. 7,440, 098, which claims benefit of U.S. Provisional Patent Application Ser. No. 60/827,837, filed Oct. 2, 2006 and U.S. Provisional Patent Application Ser. No. 60/744,246, filed Apr. 4, 2006. The entire disclosure of all of these documents is herein incorporated by reference.

BACKGROUND

1. Field of the Invention

This invention relates generally to the field of spectroscopy and spectrum analysis, more particularly, to an analysis system, tool, and method capable of performing optical or other spectral fluid analysis within a wellbore by utilizing a sample and reference channel and a Micro Mirror Array (MMA) to provide real-time scaling or normalization.

2. Description of the Related Art

A variety of systems are used in wellbore geophysical exploration and production operations to determine chemical and physical parameters of materials in the wellbore environs. The wellbore environs include materials, such as fluids, in the vicinity of a wellbore as well as materials, such as fluids, within the wellbore. The various systems include, but are not limited to, wireline formation testers, drilling formation testers, production logging systems, under-balanced drilling systems, wellbore fluid analysis systems conveyed within the wellbore, and fluid analysis and monitoring systems disposed permanently within the wellbore.

Wireline formation tester systems are used in the oil and gas industry primarily to measure pressure of a formation penetrated by a wellbore and to collect and analyze fluids from the wellbore environs to determine major constituents within the fluid. Wireline formation testing systems are also used to determine a variety of properties of the formation in the vicinity of the wellbore. These formation properties, combined with analyses of physical and chemical properties of the formation fluid, can be used to predict and evaluate production prospects of reservoirs penetrated by the wellbore.

Regarding formation fluid sampling, it is of prime importance that fluid collected for analysis represents formation fluid with minimal contamination from fluids used in the wellbore drilling operation Various techniques have been used to minimize sample contamination including the monitoring of fluid pumped through a downhole instrument or section or sections of the downhole wireline formation tester tool system until one and/or more fluid properties, such as resistivity, cease to change as a function of time.

The formation testing tool utilizes isolation elements such as straddle packers or doughnut-shaped pad packers that contain one or multiple ports These elements seal against the formation to isolate a region of the formation from the interior of the wellbore allowing the formation to be sampled in relative isolation. Fluids from within the formation are pumped directly through the port or ports from within the isolated formation and are then pumped through the formation tester tool sections via one or more flowlines. Within the tool are a plurality of instruments or sensors for analyzing the fluid. The fluid, which contains crude components (solid, liquid, and/or gas) as well as drilling mud filtrate or other contaminants, flows through the formation testing tool and is analyzed. When it has been determined that mud filtrate or other contamination has been minimized, the fluid can be retained within sample cylinders within the tool and typically returned to the surface of the earth for more detailed chemical and physical testing.

In addition to sample gathering, fluid analyses within the downhole tool typically include the determination of oil, water and gas constituents of the fluid. Sometimes the instruments and sensors are used to analyze fluid properties of the fluid from a particular region of the formation downhole and no sample is saved to return to the surface. This analysis may be used, for example, to determine connectedness of the reservoir by examining and identifying the fluids that occur in that particular compartment of the reservoir. Furthermore, it is desirable to determine the concentrations of methane, $CO_2$, $H_2S$, hydrocarbons ($C_n$, where n=2, . . . , 6+), or water, as well as certain metals within the fluids. Often, it is desirable to obtain multiple fluid analyses or samples as a function of depth within the wellbore. Operationally, it is desirable to obtain these multiple analyses and/or samples during a single trip of the tool within the well.

Formation tester tools can be conveyed along the wellbore by a variety of means including, but not limited too, a single or multi-conductor wireline, a "slick" line, a drill string, a permanent completion string, or a string of coiled tubing, Tool response data and information as well as tool operational data can be transferred to and from the surface of the earth using wireline, coiled tubing and drill string telemetry systems. Alternately, tool response data and information can be stored in memory within the tool for subsequent retrieval at the surface of the earth.

For carrying out fluid analysis, spectroscopes such as spectrophotometers, spectrometers, spectrofluorometers, or spectrum analyzers are used in numerous situations to detect and provide spectral characteristics of a test fluid, These characteristics can then be used to provide an analysis of the chemical and/or physical properties of the fluid for reservoir description and modeling, production planning, and other hydrocarbon exploration and production tasks, Spectroscopes typically utilize some form of electromagnetic radiation (EM) to perform fluid analysis. The wavelength of this EM radiation can be in the x-ray range, the gamma radiation range, the ultraviolet range, the visible range, the infrared range, or any combination of these ranges of radiation.

Prior spectroscopes are typically physically large devices due to the necessity of splitting the EM radiation into various components. Many spectroscopic systems that utilize spectrum analysis are also constrained by their ability to utilize a limited number of spectral analysis techniques and by their hardware configuration. Once built, generally the spectrum can only be analyzed temporally or spatially, but not both. Because of the typically harsh environment in which a downhole tool operates, prior downhole spectroscopes have been severely limited by the number of discrete channels they can process. Furthermore, prior spectroscopes are typically dependent upon their ability to remain calibrated as they analyze or scan. This can be very difficult in spectroscopes utilized in a downhole tool as the spectroscopes often require near constant operator interaction to adjust for changing systematic factors, and to continually check and adjust calibration to a "standard" calibration. All of these characteristics of prior systems, therefore, typically render most spectroscopes relatively unsuitable for real-time analysis of flowing fluid in a downhole wellbore environment.

In addition to formation testing systems, production logging systems, as well as permanently installed systems, are used in the oil and gas industry to identify the location, type and amount of fluid flowing through or entering a wellbore as a function of time and/or depth within the wellbore. Preferably, volume flow rates of each of oil, water and gas is measured as a function of time and/or depth. Production logs are typically used to monitor the production performance of existing wells. As well, production logs can be used to evaluate completions of newly drilled wells and to diagnose production and casing problems for older existing wells. Determination of constituents and/or properties of the fluid combined with volume flow rates of the oil, water, and/or gas constituents provide a powerful tool to make production, completion, or workover decisions about the well.

Downhole fluid analysis systems are not only used in discrete monitoring events. Systems for downhole monitoring can also be used in the oil and gas industry to monitor constituents of fluid flowing within a wellbore as a function of time and/or depth, where the monitoring time can span days or even weeks. Once again, such systems require a measure of constituents and/or properties of the fluid in the tool and under similar conditions as discussed above.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems with the art, described herein is a tool for performing, downhole analysis of a fluid the tool comprising: a port for obtaining a sample of fluid downhole; and a spectroscope, the spectroscope including: a sample channel that evaluates said formation fluid; a reference channel; and a Micro Mirror Array (MMA) comprising elements that are sequentially oriented to direct light, at sample wavelength, into the sample channel and into the reference channel; wherein response of the sample channel and response of the reference channel are combined to yield a measure of a property of said formation fluid and to correct the measure for systematic changes in the spectroscope. In an embodiment, the system determines, within the tool, chemical and physical properties of fluids that are brought into contact with a sensor.

In an embodiment, the tool may be part of a wireline formation tester system, a production logging system, a downhole fluid analysis system, a Logging While drilling (LWD) formation tester system or a Measurement while drilling (MWD) formation tester system (an LWD/MWD formation tester system).

There is also described herein a system for measuring properties of a fluid from within a wellbore, the system comprising: a tool, the tool including; a wellbore isolation element for isolating a portion of an earth formation; a port for obtaining a sample of formation fluid from said isolated portion; and a spectroscope, said spectroscope including: a light source; a Micro Mirror Array (MMA) which is used for wavelength filtering; a sample channel comprising a sampling accessory in optical contact with the fluid; a sample detector; and a reference channel comprising a reference detector; a control system that orients elements of said micro mirror array such that light at a sample wavelength is directed into said sample channel, and alternately orients elements of said micro mirror array such that the light at said sample wavelength is directed into said reference channel; and a processor for combining responses of said sample detector and said reference detector to obtain a measure of at least one property of a fluid within a wellbore and to correct the measure for systematic changes in said spectroscope.

In another embodiment, the spectroscope further comprises means for determining spectroscope dark current. In a further embodiment, the control system orients elements of the MMA such that the light is directed away from either the sample channel or the reference channel, and responses of the reference detector and sample detector, respectively, are used to determine the respective channel dark currents. In an embodiment, these measurements are used subsequently to correct spectroscope measurements for the adverse effects of background drift.

In a still further embodiment, the tool further comprises a spectroscope tool section in which the spectroscope is disposed, and a probe or port tool section through which the fluid flows into the spectroscope tool section.

In another embodiment, the tool further comprises a pump tool section, and means for isolating the probe or port tool section so that the fluid can be drawn into the tool from earth formation penetrated by the wellbore.

In an embodiment, the system further comprises a surface telemetry unit, an electronics and telemetry tool section disposed in the tool, wherein the electronics and telemetry system comprises a downhole telemetry unit, and a data conduit operationally connecting the downhole telemetry unit with the surface telemetry unit thereby allowing the measure of the property to be sent by telemetry to the surface equipment.

There is also described herein a method for measuring a property of a fluid within a wellbore, the method comprising: disposing a spectroscope within the wellbore, the spectroscope comprising a sample channel that interacts with a fluid, a reference channel, and a Micro Mirror Array (MMA) comprising micro mirror elements; sequentially orienting the micro mirror elements to direct light, at a sample wavelength, into said sample channel and into said reference channel; and combining a response of said sample channel and a response of said reference chamber to obtain a measure of a property of the fluid and to correct the measure for systematic changes in the spectroscope.

This method may be performed by a wireline formation tester system, a Logging While drilling (LWD) formation tester system or a Measurement While drilling (MWD) formation tester system (an LWD/MWD formation tester system), a production logging system, or a downhole fluid analysis system.

There is also described herein a tool for measuring properties of a formation fluid downhole within a wellbore, the tool comprising: means for isolating a portion of an earth formation; means for obtaining a sample of formation fluid from said isolated portion, means for evaluating a property of said formation fluid, and means allowing correction of systemic changes in said evaluation while said tool is downhole within said wellbore.

In another embodiment, the spectroscope utilizes an adaptive optical element such as an MMA, which is capable of providing real time scaling or normalization by utilizing two separate collection channels or light paths, and which is usable in a formation tester system.

In an embodiment, the spectroscope comprises: an MMA comprising a plurality of mirrors, each of which is switchable between a first and a second position, a light source having a spectrum, and at least two detectors; wherein the light source is spatially dispersed across the MMA in such fashion that a first group of the mirrors, can direct a first portion of the spectrum along a first light path to a first of the at least two detectors by being placed in the first position; and wherein a second position of the mirrors can direct a second portion of the spectrum along a second light path to a second of the at least two detectors by being placed in the second position.

Depending on the embodiment of the spectroscope, the light source may be a broad band light source or a narrow band light source. The first light path includes a sample to be analyzed while the second light path does not include a sample to be analyzed so the output from the second detector can be used as a reference for output from the first detector.

In an embodiment, the MMA comprises a Digital Micromirror Device (DMD).

In another embodiment, the spectroscope further comprises an input slit through which the light passes prior to reaching the MMA. Columns of the spectrum can correspond to a spectral dimension of dispersion and rows correspond to a spatial dimension of the input slit. The plurality of mirrors may be arranged into a plurality of rows and columns wherein the columns of the spectrum are incident on the MMA so as to align with the columns of mirrors or wherein the columns of the spectrum are incident on the MMA so as to align with a diagonal of the rows and the columns of the mirrors In another embodiment, the MMA performs spectral separation of the spectrum.

In another embodiment, the MMA can reversibly direct the first portion along the first and the second path and the second portion along the first and the second path in such fashion that when one of the portions is directed to the first path, the other of the portions is directed to the second path and vice-versa.

BRIEF DESCRIPTION OF THE DRAWINGS

FIG. 8 is a conceptual diagram of the dual channel processing capabilities of an embodiment of a spectroscope.

FIG. 9 provides a side (FIG. 9A), top (FIG. 9B), and end (FIG. 9C) view of the internal design of a first embodiment of a spectroscope.

FIG. 14 provides a graph of how the spectroscope can be used for dynamic filtering, FIG. 14A shows a graph before filtering while

DESCRIPTION OF THE PREFERRED EMBODIMENT(S)

The following detailed description illustrates by way of example and not by way of limitation. There is discussed herein a system for performing, downhole within a wellbore, a spectroscopic analysis of a fluid. There is also discussed a downhole tool including a spectroscope for performing such analysis of a fluid down holes within a wellbore. Basic concepts of the spectroscope are presented with the system exemplarily embodied as a formation tester system. However, in alternative embodiments the spectroscope can be embodied in systems such as, but not limited to, a production logging system and a wellbore fluid sampling and analysis system.

Figure 1:
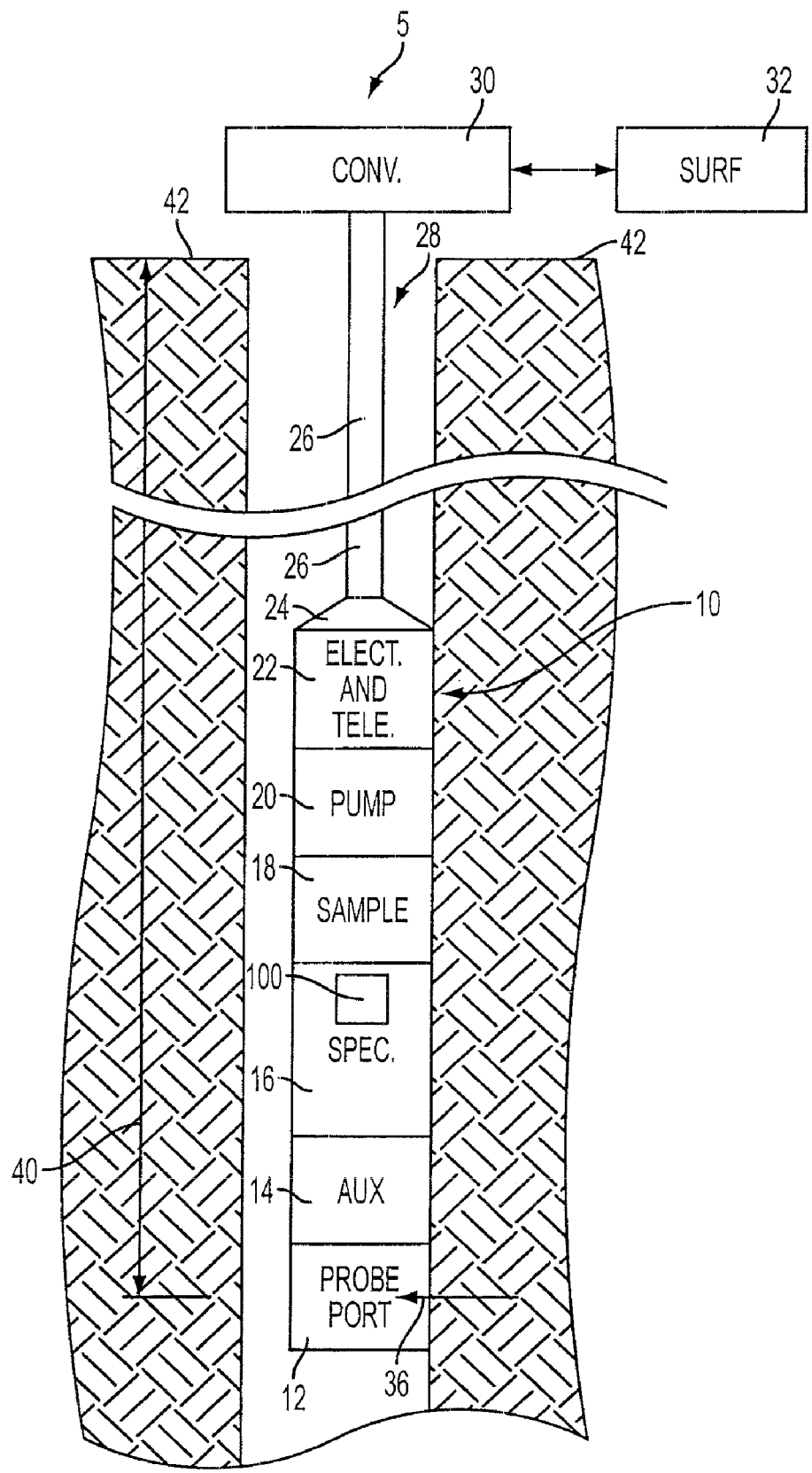
FIG. 1 provides an overview of an embodiment of a wireline formation tester system and tool operating downhole within a wellbore.

FIG. 1 illustrates conceptually the major elements of an embodiment of a formation tester system (5) operating downhole in a wellbore (28) that penetrates an earth formation (42). The embodiment of FIG. 1 is an exemplary embodiment of a more general downhole fluids analysis device. Further, the device of FIG. 1 is provided conceptually and is not intended to convey specific scale or location. The embodiment of FIG. 1 is typical of a wireline formation tester, however, the devices, systems, and methods discussed herein can be used in a variety of tools including, but not limited to, wireline formation testers, production logging tools, formation testers in use during drilling—Logging While drilling/Measurement While drilling (LWD/MWD) formation testers, downhole fluid analysis tools, or any other downhole tool known to those of ordinary skill in the art. Further, while a formation tester system as discussed herein is intended to be sent downhole and then retrieved, the systems, devices, and methods are also useable in permanent or semi-permanent downhole monitoring systems.

A formation tester system (5) generally comprises a formation tester tool (10) that is conveyed within a wellbore (28) by a conveyor (30). The formation tester wellbore instrument, or "tool" as it may be referred to herein, is denoted as a whole by the numeral (10). The conveyor means (30) is disposed at the surface of the earth, and cooperates with a tubular or a cable (26) that can serve as a data conduit between the tool (10) and the conveyor (30). The conveyor (30) is operationally connected to surface equipment (32), which may provide a variety of functions including processing tool (10) response data, controlling operation of the tool (10), recording measurements made by the tool (10), tracking the position of the tool (10) within the wellbore (28), and the like.

The formation tester tool (10) comprises a plurality of operationally connected sections which may be disposed within a housing or a drill collar. These sections may include a probe or port tool section (12), an auxiliary monitoring tool section (14), a spectroscope tool section (16), a pump tool section (20), and an electronics and telemetry tool section (22). A processor is preferably disposed within each section of the tool (10).

Again referring to FIG. 1, fluid is generally drawn into the tester tool (10) through a probe or port tool section (12). For the sole purpose of ease of discussion, it will be assumed that the probe or port tool section (12) comprises a port configured as a probe, and the section (12) will hereafter be referred to as the "probe" section (12) although that term is in no way intended to require a port configured as a probe. The probe section (12) can comprise one or more intake ports, which are not shown. Fluid flow into the probe section (12) is illustrated conceptually with the arrow indicating the draw of formation fluid (36) from within the earth structure (42) and into the probe section (12).

So as to reduce contamination of sampled fluid obtained by the probed section (12), the section of earth formation (42) will generally be isolated from the wellbore (28) so as to improve the ability to withdraw formation fluid from the earth formation (42) and to not obtain samples of fluid within the wellbore (28). During the wellbore drilling operation, the wellbore fluid and fluid within or near the wellbore formation can be contaminated with drilling fluid typically comprising solids, fluids, and other materials. drilling fluid contamination of fluid (36) drawn from the earth formation (42) may be minimized using various means of inhibiting such contamination. These include, but are not limited to, using one or more probes in cooperation with a wellbore isolation element such as a pad packer type device (not shown) that is urged against the wall of the earth formation (42). One or more probes extend through the pad into the earth formation (42). Alternately, the portion of the formation to be sampled can be isolated from the wellbore by one or more packers (not shown). A plurality of packers can be configured axially as "straddle" packers. Straddle packers and their use are disclosed in U.S. Pat. No. 5,337,621, the entire disclosure of which is herein incorporated by reference.

Still referring to FIG. 1, fluid (36) may pass from the probe section (12) through appropriate flow lines (not shown) and into the auxiliary monitoring tool section (14). The auxiliary monitoring tool section (14) can comprise one or more sensors (not shown) that can measure various physical parameters of the fluid such as, but not limited to, resistivity, dielectric potential, temperature, density, viscosity, or mass. The fluid then passes within appropriate flow lines (not shown) into the spectroscope tool section (16), where chemical and/or physical analyses are performed on the fluid while the tool (10) is disposed within the wellbore (28).

The rate of fluid flow through the tool (10) can be measured and controlled. As discussed in detail in the preceding and following sections of this disclosure, a spectroscope such as spectroscope (100) (discussed later) is deployed within the spectroscope tool section (16) or any other suitable location and performs optical or alternately other types of spectral measurements on the fluid (36) from which concentrations of constituents and/or other chemical or physical properties of the fluid (36) are determined. These measurements may also be processed to identify and to determine chemical and/or physical properties of the fluid (36). The spectroscopic measurements and chemical and/or physical properties can be preferably made in real-time and at a plurality of axial positions or "depths" during a single trip of the tool (10) in the wellbore (35). Furthermore, a plurality of measurements can be made at a single depth during a single trip of the tool (10) in the wellbore (35). The spectroscope (100) can also be deployed as part of a permanent completion within the wellbore (28). The spectroscope (100) can be deployed by any means known to those ordinarily skilled in the art and is not intended to be limited to the exemplary methods described herein.

In one embodiment the spectroscope may be comprised of a Micro Optical Electro Mechanical System (MOEMS) which is fabricated typically from a plurality of micro mirror devices. A MOEMS device for this purpose includes, but is not limited to, any commonly used description for these devices such as DMD, DLP, or MMA. For purposes of clarity all of these common names will be referred to as a Micro Mirror Array (MMA) for subsequent discussion, In addition to other benefits, an MMA can be used to provide real-time instrument sensitivity calibration, dark current correction, and corrections for system drift including gain and baseline drift. Construction of the spectroscope is robust making it suitable for use in typically harsh wellbore conditions. In addition, the spectroscope is adaptable to a variety of wellbore conditions, and versatile in operation as will become apparent in subsequent sections of this disclosure.

Again referring to FIG. 1, the fluid may be directed to the sample tool section (18), via appropriate flow lines (not shown), after passing through the spectroscope tool section (16). Fluid samples can be retained within one or more sample containers within the sample tool section (18) for return and to the surface for additional analysis. The surface is typically the surface of earth formation (42) or the surface of any water covering the earth formation (42), as may be the case when the wellbore is generated in an ocean floor or similar structure.

Fluid may be drawn into the probe tool section (12), pumped through the auxiliary and spectroscope tool sections (14) and (16), respectively, optionally pumped into sample containers within the sample tool section (18), and optionally purged into the wellbore (28) by one or more pump tool sections (20) disposed in the tool (10). Power for all of the previously discussed sections of the tool (10), operation of the tool and the various elements within the tool, and transfer of data and commands into and out of the tool, may be provided and controlled through the electronics and telemetry tool section (22). A processor within the spectroscope tool section (16) is preferably used to process data measured by the spectroscope tool section (16), and to control operation of the spectroscope within the spectroscope tool section, as will be subsequently discussed. The fluid flow paths described are exemplary and are not intended to limit the methods by which the tool (10) can be deployed as sections can be used in alternative orders and fluid flow need not be linear.

Once again referring to FIG. 1, the upper end of the tool (10) may be terminated by a connector (24). The tool (10) may be operationally connected to a conveyor (30) disposed at the surface by means of a tubular, cable (26), or similar structure designed to interconnect. More specifically, the lower or "wellbore" end of the cable (26) is operationally connected to the tool (10) through the connector (24). The upper or "surface" end of the cable (26) is operationally connected to the conveyance means (30). In an embodiment, the cable (26) can function as a data conduit between the tool (10) and equipment disposed at the surface.

In an embodiment, the tool (10) is a logging tool element of a wireline formation tester system, and the cable (26) is a multi-conductor wireline logging cable and the conveyance means (30) is a wireline draw works assembly comprising a winch. In another embodiment, the tool (10) is a component of a measurement-while-drilling or logging-while-drilling system, the cable (26) is a drill string and the conveyor (30) is a rotary drilling rig. In a still further embodiment, the tool (10) is an element of a coiled tubing logging system, the cable (26) is coiled tubing and the conveyor (30) is a coiled tubing injector. In a still further embodiment, the tool (10) is an element of a drill string tester system, the cable (26) is again a drill string and the conveyor (30) is again a rotary drilling rig. Other embodiments of the tool (10), cable (26) and conveyor (30) would be readily understood by a person of ordinary skill in the art.

Again referring to FIG. 1, surface equipment (32) may be operationally connected to the tool (10) through the conveyor (30) and the structure (26). The surface equipment (32) may comprise a surface telemetry element, which communicates with the downhole telemetry unit disposed within the electronics and telemetry tool section (22). The cable (26) functions as a data conduit between the downhole and surface telemetry elements. The surface unit (32) may also comprise a surface processor that optionally performs additional processing of data measured in the spectroscope tool section (16).

In another embodiment, the surface processor may also cooperate with a depth measure device (not shown) to track data measured by the tool (10) as a function of depth (40) within the wellbore at which it is measured, or the surface equipment (32) may comprise recording means for recording "logs" of one or more parameters of interest as a function of time and/or depth. The surface equipment (32) may comprise any data or mechanical-based machine, circuitry, computer, or other device to perform any desired function.

While this disclosure will also generally refer to the device within the spectroscope tool section (16) of the tool (10) as a "spectroscope" it should be recognized that this term is not being used to refer to a particular type of spectral evaluation device but is intended to refer generally to a class of devices used in conjunction with the review, evaluation, or analysis of spectrums. It is not required that all spectrum evaluations or analysis devices used in a spectroscope be used in this device. The device can be used in any kind of real-time or other process spectroscopy monitoring including, but not limited to, optical monitoring, spectrophotometry, spectrofluorometry, spectrum analysis, spectrocolorimetry, and spectroradiometry.

Generally, the spectroscope (100) includes optical components to shape, manipulate, or route incident light to targets of interest, spectrally disperse incoming light, image the dispersed light onto a spatial, spectral, or temporal filtering device, direct the filtered light onto, into, or around (bypassing) a sample, and then direct the light to some type of optical detector. The spectroscope (100) of the present disclosure provides for multiple detectors each of which is associated with its own optical channel, or light path. In the depicted embodiments, two channels are shown as this is generally the preferred number, however, in alternative embodiments more may be used.

In addition to determining chemical and/or physical properties of the fluid, the spectroscope (100) embodied in the tool (10) may be capable of real-time dark current correction and pre-scan or post-scan referencing of any illumination source. Dark current is also known as dark noise and by other common names.

The spectroscope (100) may be controlled by a processor disposed preferably within the spectroscope tool section (16). In an embodiment, commands can be preprogrammed in the processor. Alternately, commands can be input from the surface equipment (32) in real time such as via the previously discussed telemetry system. The processor controls the operation of the spectroscope (100) and, in an embodiment, can be used in processing results obtained from the spectroscope's (100) response to fluid.

Embodiments of a spectroscope (100) which may be used in the tool (10) are further described in U.S. patent application Ser. No. 11/696,005, the entire disclosure of which is incorporated herein by reference.

Figure 2A:
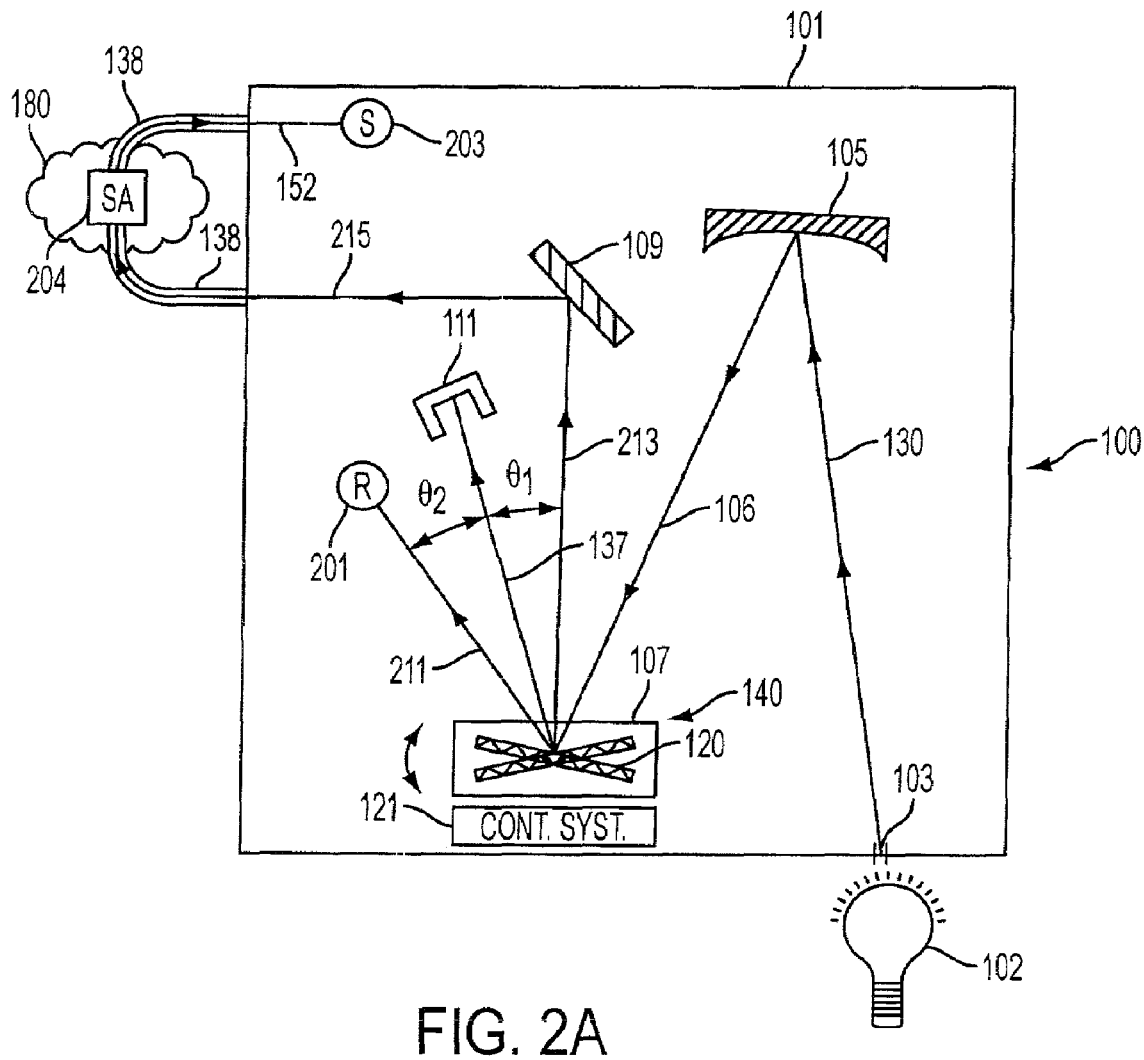
FIG. 2A is a conceptual diagram of an embodiment of a spectroscope utilizing multiple channels disposed within the spectroscope tool section of an embodiment of a tool.
Figure 2B:
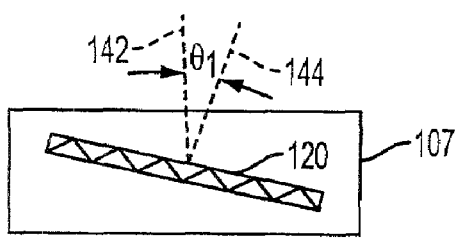
FIG. 2B illustrates a single micro mirror of a Micro Mirror Array (MMA) oriented to direct light into the sample channel of the spectroscope.
Figure 2C:
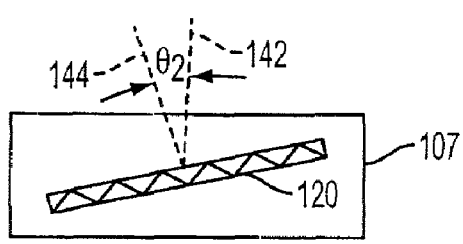
FIG. 2C illustrates a single micro mirror of an MMA oriented to direct light into the reference channel of the spectroscope.
Figure 3:
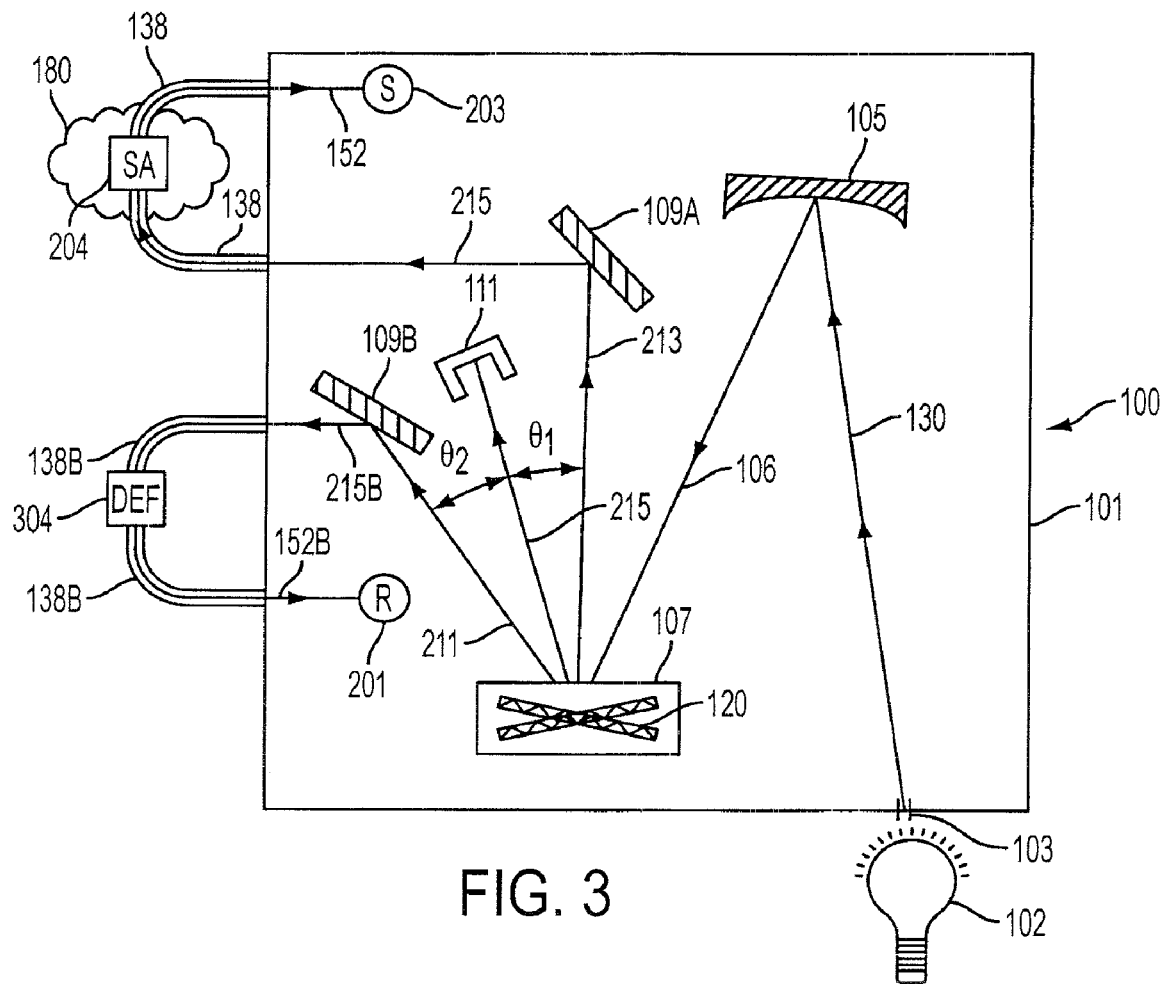
FIG. 3 is a conceptual diagram of another embodiment of a spectroscope utilizing sample and reference accessories.
Figure 4:
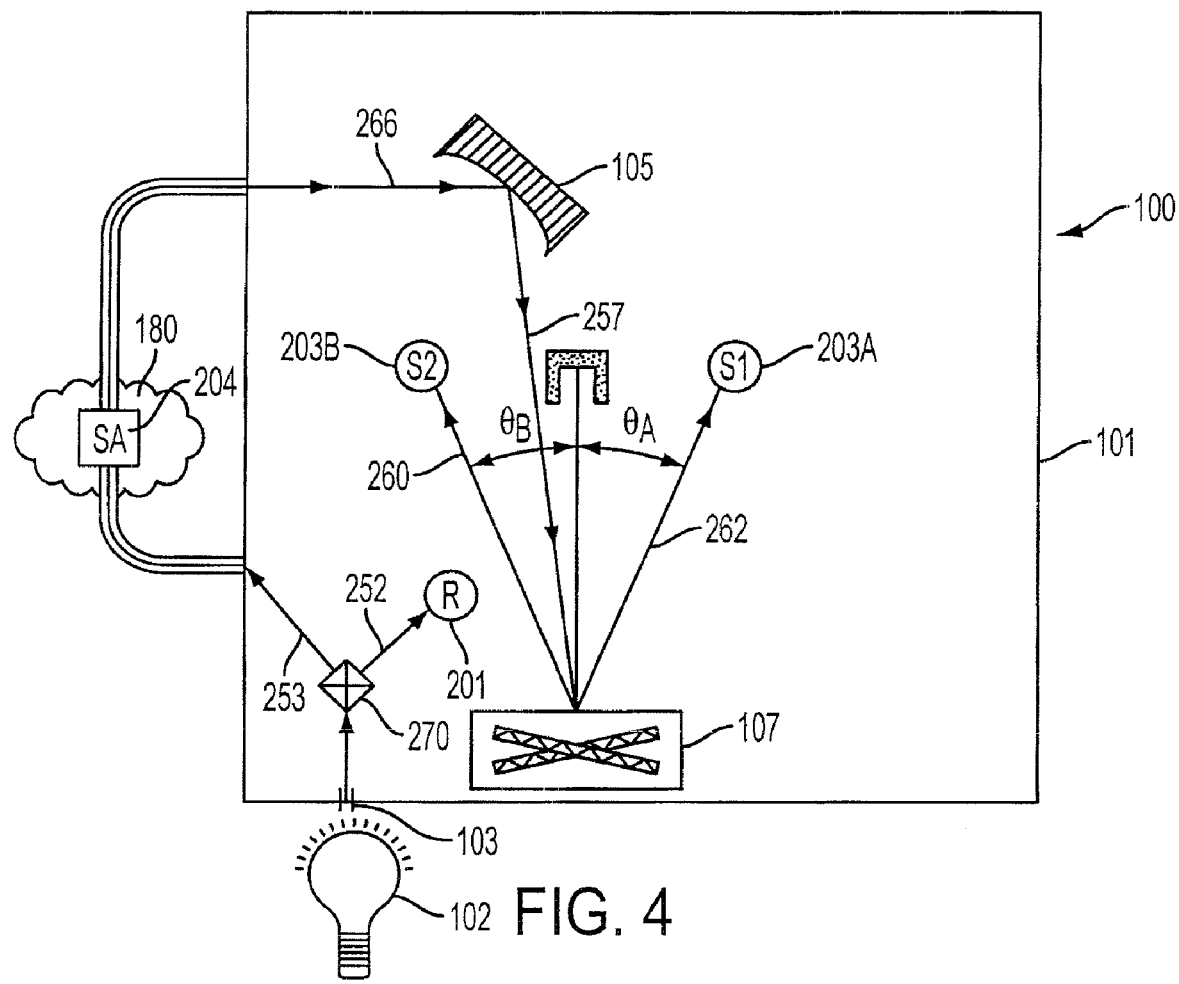
FIG. 4 is a conceptual diagram of another embodiment of a spectroscope utilizing a light source incident on a sample prior to being incident on an MMA.

Referring to FIGS. 2 through 4 which provide for various embodiments of spectroscope (100) which may be used in different embodiments of tool (10), light is generally delivered to the spectroscope (100) via optical fiber or free-space delivery from a light source (102). The optical fiber delivery methodology is generally preferred. The light source (102) will generally be operable in typically harsh wellbore (28) conditions and will be located within the spectroscope tool section (16), but that is by no means required. The light source (102) may be provided by a single source such as, but not limited to, tungsten filament, metal halide, incandescent light, or any source known or yet to be discovered. Light can also be obtained by any combination of sources including, but not limited to, light emitting diodes (LED's), lasers, arc sources, and the like.

Further, while the embodiments of the spectroscope (100) discussed herein are capable of manipulating all wavelengths of electromagnetic radiation, the remaining discussion will focus on the wavelength ranges of the ultraviolet, visible, near infrared and mid infrared regions as the electromagnetic spectrum being used. Further, the radiation will be referred to using the term "light" even though the spectrum is intended to include wavelengths outside the bounds of visible light in at least some embodiments.

The light source (102) will generally comprise a broadband light source emitting a number of different wavelengths of light simultaneously such as, but not limited to, natural solar radiation, a tungsten filament, or any combination of narrow band sources. In an alternative embodiment, the light source (102) may comprise a single narrow band or single wavelength source such as, but not limited to, light emitting diodes or lasers; an electrically charged gas such as neon that emits a narrow band or a number of narrow bands, or any other light source known to those of ordinary skill in the art. The light can be provided to the spectroscope (100) device discussed herein by any method known to one of ordinary skill in the art including, but not being limited to, being reflected, refracted, focused, or diffused prior to reaching the spectroscope (100).

In FIGS. 2A, 2B, and 2C the two detectors (201) and (203) which are pail of the spectrometer are accessed through one of two optical channels (211) and (213). One optical channel (213) is capable of directing light to a sampling accessory (204), such as, but not limited to, a fiber optic probe, a cuvette assembly, or another device as would be understood by one of ordinary skill in the art. The second optical channel (211) is generally used as an optical reference channel for calibration and therefore does not include a sampling accessory (204) However, in alternative embodiments the second optical channel (211) could be used as a secondary data channel in some applications, such as spectroradiometery or spectralfluorimetry, to improve Signal-to-Noise (S/N) and/or to enhance data sampling rates in which case a sampling accessory could be provided. In this embodiment, one light path is therefore used to interrogate the sample, while the other is directed to bypass (not interrogate) the sample.

Throughout this disclosure these channels (211) and (213) or light paths may be referred to as a "sampling channel" and a "reference channel." This is to refer to the fact that the sample channel (213) is generally used when the electromagnetic radiation is directed through a sample while in the reference channel (211) the light is generally not directed through that sample, but is used for reference. One of ordinary skill in the art, however, would recognize that the channels could be reversed in roles depending on embodiment and none or both of the channels could include sample depending on the desired operation. For example, the reference channel (211) could include a gas correlation cell in an embodiment.

FIG. 2A provides a block diagram showing the conceptual layout of an embodiment of a spectroscope (100) of the present invention which, in an embodiment, is disposed within the spectroscope tool section (16) of an embodiment of the tool (10). The device of FIG. 2A generally comprises a housing (101) into which other components are placed to shield them from ambient light. The housing (101) includes an input aperture (103) such as a slit which will serve to provide the incident light to be used in the spectroscope. The use of a slit will result in the light generally having a spread spectrum of height depending on the height of the slit. The light source (102) may alternatively be provided in the housing (101) in which case it would have a predefined path formed in the housing (101) for forming a light input of desired shape and size, The incident light source (102) will generally provide light (130) of a number of different wavelengths (broadband light). The incident light that passes through the slit (103) is directed onto a grating (105), prism, or other surface capable of separating the light into its spectrum, which is used to spatially disperse light as a function of wavelength.

This light is then projected onto an adaptive optical element which is some form of device which can change its surface or other optical property to change the direction that light incident on it is directed. In an embodiment, this comprises an array of individually moveable mirrors. In the preferred embodiment, this is a micro-opto-electromechanical (MOEM) device comprising a Micro Mirror Array (MMA) (107). In an embodiment, the MMA (107) comprises a Digital Micromirror Device (DMD) such as those manufactured by Texas Instruments. The MMA (107) will generally comprise a large number of mirrors of very small size which are arranged in a recognized pattern. In most embodiments, this will be a grid. The mirrors on the MMA (107) are generally independently positionable via a control system, (not shown) to at least two different positions. The MMA mirrors also can move between at least those two positions when such movement is requested by the control system. In the depicted embodiment where the MMA is a DMD, the two positions are generally +10° and −10° from a predetermined horizontal position (0° position).

Figure 8B:
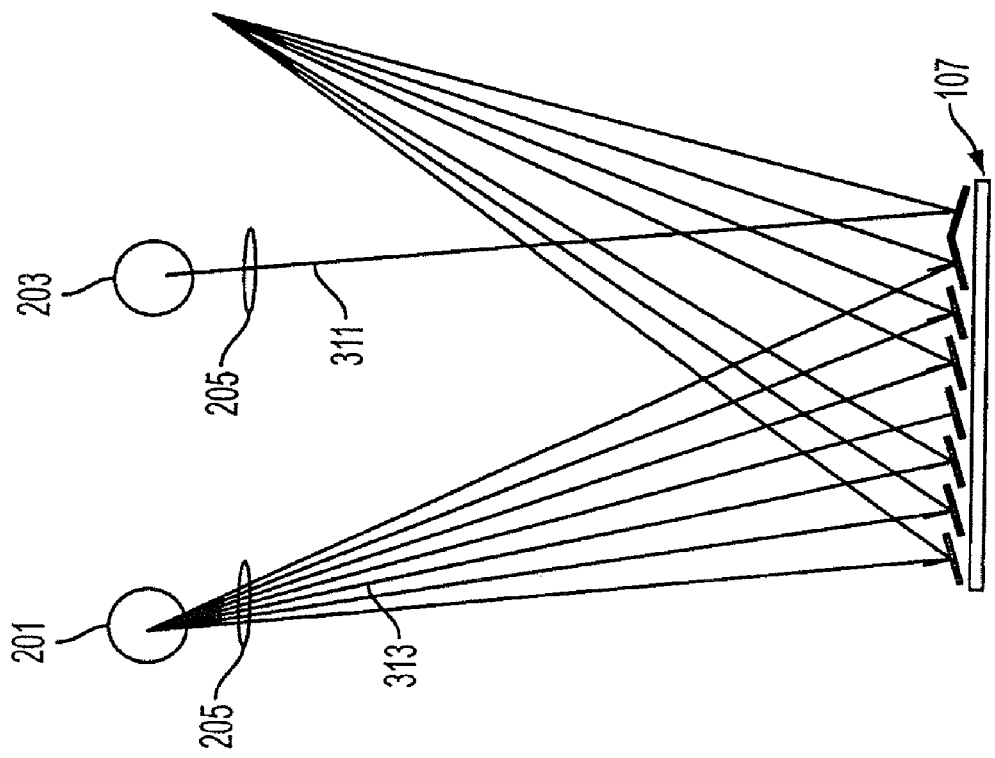
FIG. 8B shows the first wavelength directed to the sample channel with all other wavelengths directed to the reference channel.
Figure 8A:
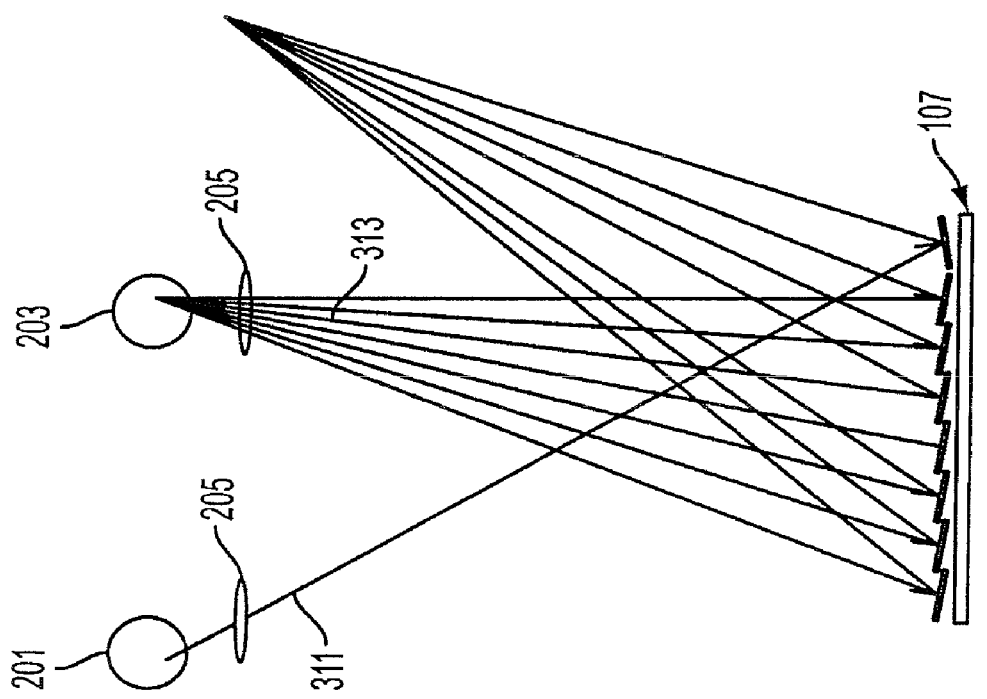
FIG. 8A shows a first wavelength directed to the reference channel with all other wavelengths directed to the sample channel.

Details of the MMA are discussed in a subsequent section of this disclosure and illustrated in FIGS. 8A and 8B. For simplicity. FIGS. 2A, 2B and 2C show only a single ray trace incidental on a single mirror (120) of the MMA (107).

Alternate means can be used to form the dispersed light (106). As an example, the grating (105) can be replaced by a prism to redirect and to disperse light from the light source (103) onto the MMA device (107). Another alternate dispersed light source (not shown) can comprise an array of narrow beam light sources such as, but not limited to, light emitting diodes or lasers. Each element of the array is focused onto the MMA device (107).

Again referring to FIGS. 2A, 2B, and 2C, a single mirror (120) of an MMA (107) is shown to illustrate the basic operational concepts of the spectroscope (100). The single mirror (120) is oriented within the MMA (107) in at least two discrete positions so that some or all of the various wavelengths of light (106) incident on the single mirror (120) is directed into two different channels, which are defined as the "sample" channel and the "reference" channel.

Referring to both FIGS. 2A and 2B, the single mirror (120) is oriented at an angle $\Theta_1$, where $\Theta_1$ is defined as the angle between the normal (142) of the MMA (107) and the normal (144) of the single mirror (120). This orients the spectroscope (100) in the "sample" channel, wherein light is reflected from the single mirror (120) to a mirror (109), as illustrated conceptually by the ray path (213).

As illustrated in FIGS. 2B and 2C, the mirrors will generally be independently arranged at two different states having different angular positions. Generally, these two different positions may be angularly symmetrical about a midpoint location simply for position stability. For example, if the midpoint was classified as a 0° state, the two positions can be a +X° and −X° degree state from the 0° position. The midpoint is also preferably chosen to correspond to the position where the individual mirror on the MMA is arranged generally parallel to the substrate of the MMA.

The mirror (109) reflects light, as indicated conceptually by the ray path (215), out of the spectroscope housing (101) and into a light guide (138) such as a fiber optic cable. The light guide (138) includes a sampling accessory (204) which is in contact with a fluid (180) to be analyzed. The optical-response of the fluid as measured by the sampling accessory (204) is returned via a light guide (138) to the spectroscope (100) and into a sample detector (203), as indicated conceptually by the ray path (152). Spectroscopic response of the sample detector (203) to constituents of the fluid (180) will be discussed in a subsequent section of this disclosure. It should be recognized that ray paths (215) and (152) are simply continuations of ray path (213), but are indicated with separate references for clarity The sampling accessory (204) can be, but is not limited to, a dip accessory, a reflectance accessory, a transmittance accessory, a fluorescence accessory, an Attenuated Total Reflectance (ATR) accessory, an extractive flow cell, or any other sampling or monitoring device known to those familiar to the art.

The spectroscope can use Conventional Raster Scanning (CRS), Hadamard Transform (HT), Fourier Transform (FT), or any other encoding methods known to those familiar to the art.

Now referring to both FIGS. 2A and 2C, the single mirror (120) is oriented at an angle $\Theta_2$, where $\Theta_2$ is defined as the angle between the normal (142) of the MMA (107) and the normal (144) of the single mirror (120). This orients the spectroscope (100) in the "reference" channel, wherein light is reflected from the single mirror (120) to a reference detector (201), as indicated conceptually by the ray path (211). The reference channel allows the sample channel response to be corrected in real time for drift and other systematic changes as will be discussed subsequently.

Referring to FIGS. 2A, 2B and 2C, the single mirror (120) can be oriented so that the normal (142) of the MMA (107) is coincident with the normal (144) of individual mirrors of the MMA This orients the spectroscope (100) so that light is directed into an optical trap (111), as indicated conceptually by the ray path (137). This orientation is referred to as the "zero degree" state, and could be used as one method for correcting the sample and reference channels for dark current.

Other methods of dark current measurement are easily envisioned by directing the MMA mirrors away from the sample or reference channels as they are being measured.

Using the above nomenclature to define the orientation of the MMA (107) (see FIGS. 2B and 2C), $\ominus_1$ for the sample channel is preferably about +10°, $\ominus_2$ for the reference channel is preferably about −10°, and the angle zero degree state is $\ominus=0°$. Note that the use of +10 and −10 degrees is for illustrative purposes only and that the actual angles will depend on the device used and while such angle may be used in an embodiment, generally there are +X° and −X° states. While the depicted embodiment utilizes mirrors that have three discrete states (+X°, 0, −X°), alternative embodiments may utilize an MMA with numerous mirror positions, such as an analog driven MMA or an MMA with only 2 discrete positions (such as those shown in FIGS. 2B and 2C) with no 0° state. The spectroscope can use the position of the mirrors, either singly or in any combination, to achieve the sample, reference and dark current measurements.

Figure 10:
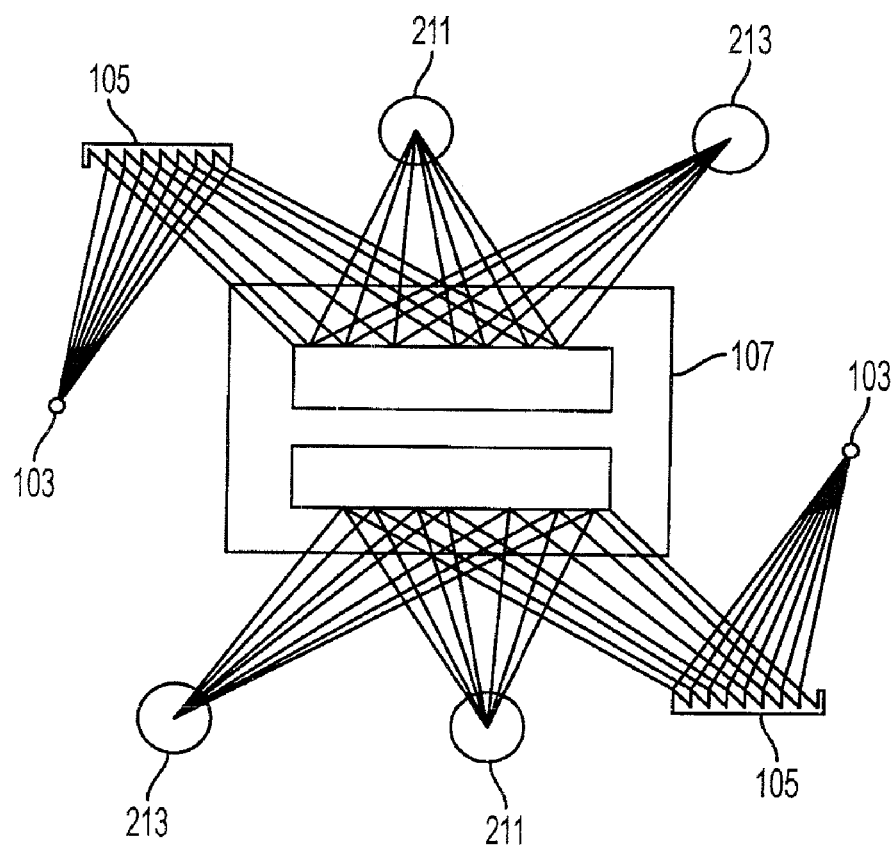
FIG. 10 provides a conceptual diagram of the internal design of a spectroscope using two separate inputs and measuring two samples.

FIGS. 9A, 9B, and 9C provide a series of general block diagrams of embodiments of the spectroscope shown in the conceptual diagram of FIG. 2A. Not shown for clarity are the optical elements (205) used to image the spectrally processed light (i.e. post MMA (107)) into the individual channels These figures are provided to show a possibility for how an actual optical path using the MMA (107) and two sample channels can be accomplished. FIG. 10 provides for a conceptual layout of a spectroscope which includes two light inputs and essentially provides for four light paths by providing two spectroscopes (100) in the same housing (101) and using the same MMA (107).

Figure 5:
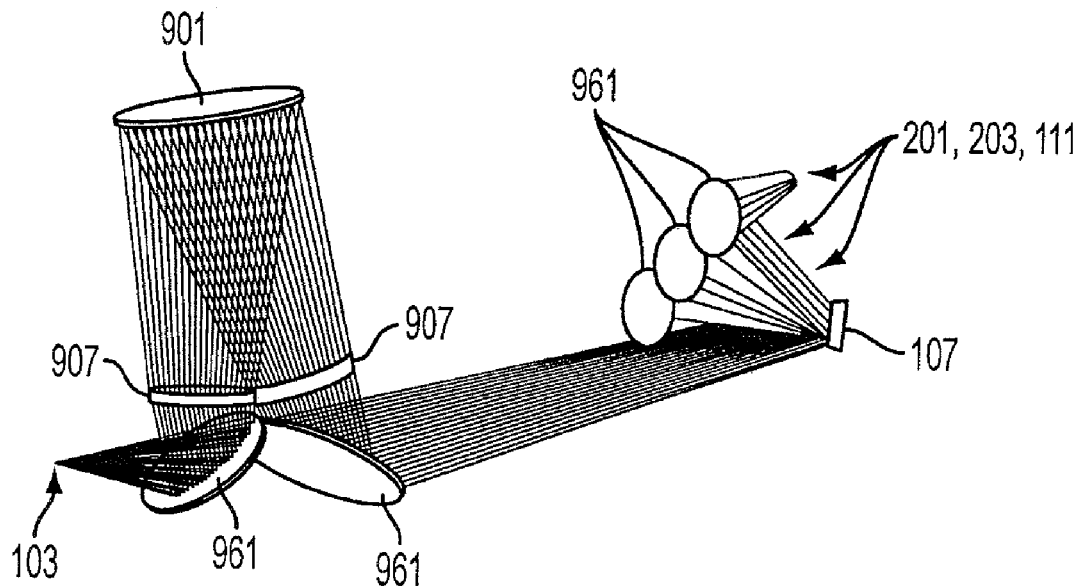
FIG. 5 provides for an embodiment of an optical path.
Figure 6:
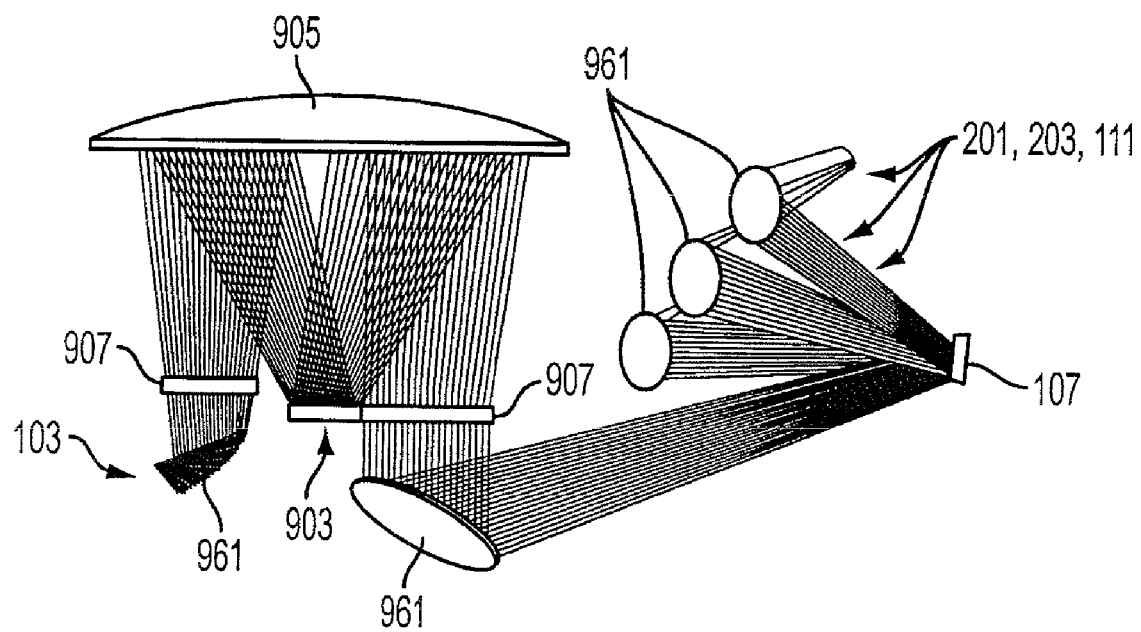
FIG. 6 provides for an alternative embodiment of an optical path.
Figure 7:
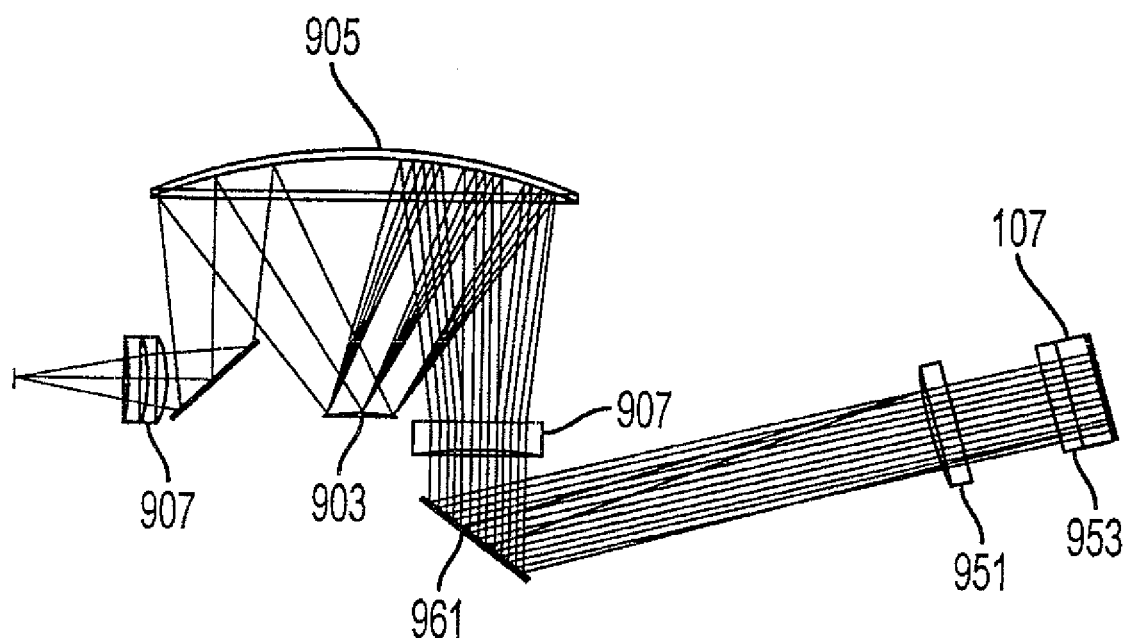
FIG. 7 provides for another embodiment of an optical path.

Light incident on the MMA (107) will be routed from the slit (103) and grating (105) and potentially, may be further manipulated to improve, among other things, its shape, dispersion, or intensity. FIGS. 5 through 7 provide for a number of embodiments of a spectroscope showing light path manipulation prior to the MMA (107). The various embodiments can include concave diffraction gratings (901), convex diffraction gratings (903), concave mirrors (905), or lenses (907) to manipulate the light spectrum prior to it being incident on the MMA (107). In the embodiments of FIGS. 5 through 7 there are also included a number of other light handling objects prior to the MMA including relay mirrors (961), lenses (907), and a telecentric lens (951) which is added to make all light incident on the MMA (107) normal (perpendicular) to the MMA (107) face. There may also be included a filter (953). In this configuration, the spectrometer (100) can be used to recombine the light into the reference channel (211) or sample channel (213). The design of FIG. 7 can provide for an athermal spectrometer (100) which can provide for improved resolution and accuracy of resultant readings over a large temperature range.

FIG. 3 is a conceptual illustration of another embodiment of the spectroscope (100). Many of the elements and related fight ray paths are the same as those depicted in FIG. 2A and for brevity are not redefined. There are, however, significant new elements in the embodiment. The reference channel comprises a second mirror (109B) in addition to the mirror in the sample channel, which is now denoted as (109A). The sample channel configuration and operation is essentially the same as the sample channel depicted in the embodiment of FIG. 2A, when the single mirror (120) of the MMA (107) is oriented at angle $\ominus_1$. Light passes from the single mirror (120) of the MMA (107), and is reflected by the mirror (109A) as illustrated conceptually by the ray paths (213) and (215). Light then passes out of the spectrometer housing (101) and onto a light conduit (138), such as a fiber optic cable. The path (215) passes into a sample accessory (204) which is in contact with a sample (180) to be analyzed. The optical response of the sample accessory (204) is returned via the optical conduit (138) to the spectroscope (100) and into a sample detector (203), as indicated conceptually by the light path (152).

Again referring to FIG. 3, when the single mirror (120) of the MMA (107) is oriented at angle $\ominus_2$, light is reflected from the single mirror (120) to the mirror (109B), as illustrated conceptually by the ray path (211). The mirror (109B) then reflects light, as indicated conceptually by the ray path (215B), out of the spectroscope housing (101) and onto a light conduit (138B) such as a fiber optic cable. The light path (215B) passes into a reference accessory (304), which is in contact with a reference sample to be analyzed. The optical response of the reference accessory (304) is returned via the optical conduit (138B) to the spectroscope (100) and into a reference detector (201), as indicated conceptually by the light path (152B).

As stated previously, light in the reference channel is directed through a reference accessory (304) via the light conduits (138B). The reference accessory (304) can comprise a holmium standard, gas correlation cell, and/or any other calibration, reference material or standard known to those familiar to the art.

Still referring to FIG. 3, the MMA (107) alternately operates in the sample and standard channels. Corresponding spectroscopic responses are measured in the fluid (180) by sample accessory (204), and in the reference accessory (304). Since, by definition, the spectroscopic response of the reference accessory is a "reference standard", the spectroscopic fluid response can be compared continuously with the reference accessory spectroscopic response, and any systematic variation within the spectroscope (100) can be measured and used to correct fluid response for these variations, which include gain and base line drift.

FIG. 4 is another conceptual embodiment of the spectroscope (100). Many of the elements and related light ray paths are similar to those depicted in the prior embodiments and, for brevity, will not be redefined. There are, however, also significant new elements in this embodiment. The reference channel comprises a first light path (252) direct from a splitter (270) on the light source (102) and slit (103). The second light path (253) from the splitter (270) is sent to the sampling accessory (204). The return light (256) from the sampling accessory (204) is directed onto a grating (105) that is used to disperse the light as a function of wavelength. This dispersed light, represented conceptually by the ray path (257), is projected on an MMA device (107). A single mirror (120) is again shown for purposes of illustration. The MMA device (107) is used to filter the light based on wavelength. This filtered light is subsequently directed from the MMA device (107) via path (262) to a first sample detector S1 shown at (203A), or via a path (260) to a second sample detector S2 shown at (203B). A dark current measurement for the first sample detector (203A) can be made by projecting all light away from this detector and at an angle $\ominus_B$ into the sample detector (203B) via the light path (260). Conversely, a dark current measurement for the second sample detector (203B) can be made by projecting all light away from this detector and at an angle $\ominus_A$ into the sample detector (203A) via the light path (262). Measurements from both sample detectors S1 (203A) and S2 (203B) can be used for additional calibration information, to reduce acquisition time, or to minimize the effects of noise and/or drift.

Figure 11A:
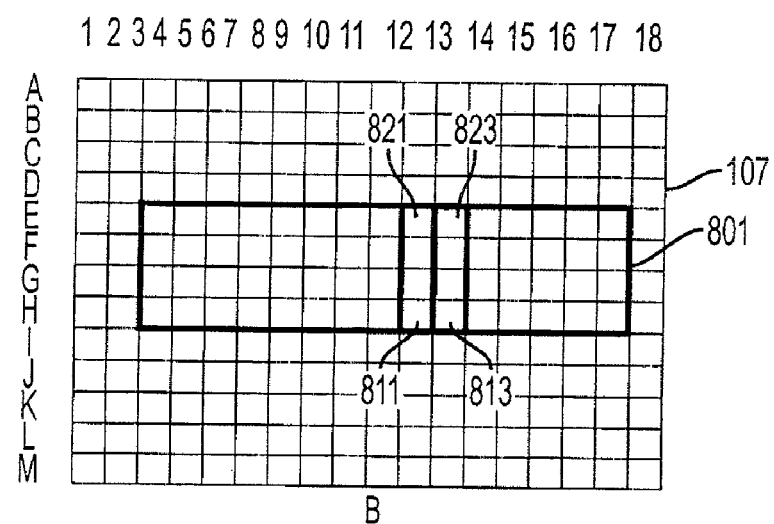
In FIG. 11A, the spectrum is aligned with the MMA, while in FIG. 11B the spectrum is angled across an MMA.
Figure 11B:
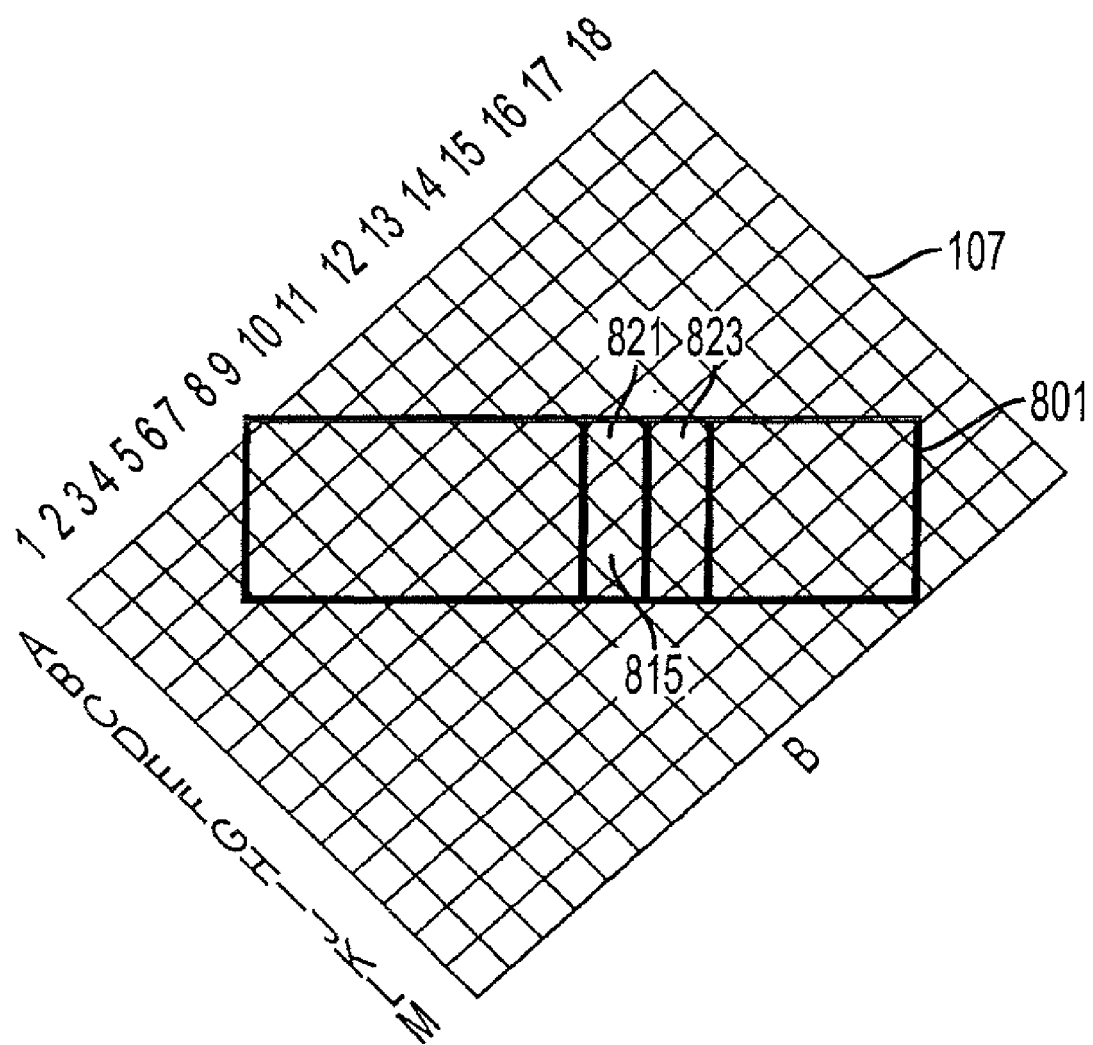
FIG. 11 provides for positioning of a spectrum on an MMA.

The light incident on the MMA (107) is generally in the form of a spread spectrum. That is, the component wavelengths of the light will be spatially separated from each other by being bent through different angles at a time prior to being incident on the MMA (107). Such light will generally have a spectrum going from light having longer wavelength (red and infrared) to light being shorter wavelength (violet and ultraviolet). The spectrum of light (801) is shown as the dark outline rectangle (801) in FIGS. 11A and 11B with the one end representing shorter wavelength light and the other end longer wavelength light. It should be recognized that points directly vertical of each other in FIGS. 11A and 11B are the same wavelength. Therefore making "rows" in the spectrum correspond to the spatial dimension of the input slit, while "columns" in the spectrum correspond to the spectral dimension of dispersion.

The MMA (107) is positioned in the housing (101) so that some or all of the various wavelengths incident on the MMA (107) are directed into the two different channels (211) and (213) or (260) and (262) depending on embodiment. For simplicity, the discussion will refer to channels (211) and (213) although channels (260) and (262) could be used instead, depending on embodiment. Each channel is associated with a detector (201) or (203) based on the positioning of the various mirrors of the MMA (107). Light routing is dependent on the specific MMA (107) mirror position relative to the incident radiation. That is, the wavelengths are "spectrally" filtered by the MMA (107) between the light channels (211) and (213). In order to direct specific wavelengths of the incident light within the appropriate channel (211) or (213), devices such as mirrors (961) can be placed in the various paths to direct the wavelengths incident on them as appropriate for that channel (211) or (213).

It is important to recognize that the MMA (107) does not act as a beam splitter or other device which sends part of the intensity down each path. Instead, the MMA (107) sends a portion of the spectrum down each path exclusive of the other. For example, the MMA (107) could send the red, orange, yellow, and green portion of the visible spectrum down one path and the blue, indigo, and violet portion of the same spectrum down the other path. This would mean that if the first path is reference channel (213), detector (203) would not have any blue, indigo or violet incident thereon at that time.

Alternatively or additionally, a series of order sorting filters, folding mirror's, and/or collimating lenses or focusing lenses (205), can be utilized to collect and image polychromatic, or monochromatic, light from the MMA (107), onto the appropriate detectors (201) or (203) for spectral processing. One should recognize that the embodiment of FIG. 7 allows for mirror's and other components to be used for a number of different purposes depending on whether light is incident on, or reflected from the MMA (107). In another embodiment, the spectrum incident on the MMA (107) can be temporally structured or spatially filtered in addition to or instead of the spectral filtering discussed.

Detectors (201) and (203) may measure any form or spectrum of light and, in an embodiment, detectors (201) and (203) utilize two single element photodiodes (PDs) as detectors. In an alternative configuration the detectors (201) and (203) could utilize two-dimensional (2D) charge coupled devices (CCDs) or photo diode arrays (PDAs). In still further embodiments, the detectors (201) and (203) comprise, but are not limited to Photo Multiplier Tubes (PMTs), Avalanche Photo Diodes (APDs), CMOS detectors, Bolometers, any other detector known to those of ordinary skill in the art, or any combination of these detectors.

In the various embodiments discussed herein, the spectroscope (101) is preferably attached to a sampling accessory (204) which allows one channel of light to interact with a test sample and then to return the output radiation to the sample detector (203) and eventually the control system. The sampling accessory (204) could be, but is not limited to, a fiber optic based accessory, a transmission dip probe, a reflectance probe, a fluorescence probe, an extractive flow cell, other sampling devices known to those of ordinary skill in the art, or any combination of sampling devices.

FIGS. 8A and 8B illustrate a conceptual drawing of a potential sampling mode of the spectroscope (100) of FIG. 2A. In FIGS. 8A and 8B, the MMA (107) is used as a spectral filter, with sampling occurring using one or more narrow bands of radiation at a time. FIG. 8A illustrates spectral filtering where a single narrow band of radiation (or even single wavelength) is used to probe the sample. The selected band is narrow band (311). In FIG. 8A, this band (311) would be traveling down the reference channel (211) and is therefore incident on the reference detector (201) while the remaining bands (313) are traveling down sample channel (213) and are imaged on the sample detector (203). Therefore, in this situation, the band (311) is not incident on the sample but is bypassing the sample. Since this band (311) is desired for sample interrogation, the signal generated by the band (311) at the reference detector (201) in this situation therefore represents a "non-sample" signal which can be used as a reference. The output of the sample detector (203) in this arrangement is being generated from a portion of the spectrum which may or may not be of interest. In particular, the intensity, dispersion, wavelengths, bandwidth, or any other characteristic of the band (311) may be detected by detector (201). That is, a base or reference determination of the band (311) may be established.

In FIG. 8B the band (311) is now directed down the sample channel (213) to the sample detector (203) with the remaining bands (313) directed down the reference channel (211) to reference detector (201). Now the output of sample detector (203) is of interest as the sample is being interrogated by the desired spectrum. The percent transmission or absorbance or other measurable values can be calculated based on measurements from both the sample and reference channels by comparing the output of the detectors (201) and (203). As should be apparent, because the switch between the two channels having the spectrum of interest can occur relatively quickly and repeatedly, the output of the reference detector (201) can be used to normalize the output of the sample detector (203) to provide for a scaled reading. So as to provide for the most accurate referencing, the two detectors (201) and (203) will generally be similar so that the output of the light interacting with the sample and not interacting with the sample are incident on similar detectors.

As should be apparent from FIGS. 8A and 8B, the switching of the band (311) from reference detector (201) to sample detector (203) (and the corresponding movement of bands (313)) is accomplished by adjustment of the state of the individual mirrors in the MMA (107). In particular, referring to FIGS. 11A and 11B, the spectrum incident on the MMA (107) is spread across the mirrors of the MMA (107) so that different wavelengths are incident on different portions of the MMA (107) generally with an individual wavelength, or small wavelength band being incident on each mirror in the array as shown. Each individual mirror component of the MMA (107) can be adjusted independently between at least the two different states as previously discussed. This allows for each of the bands (311) and (313) in FIGS. 8A and 8B to be independently sent to either the reference (201) or sample (203) detector simply by a selected arrangement of the mirrors.

The incident light is preferably directed toward the MMA (107) in such a way that the change in each mirror, or more particularly changes in a row, column or diagonal of mirrors can direct a particular wavelength or narrow band of wavelengths to a particular path Two different methodologies for this are shown in FIG. 11. In FIG. 11A, the spectrum (801) is incident on the MMA (107) grid so as to generally align each frequency of light with a column (or row) of mirrors. For reference, column (811) in this case is generally aligned with a small band of wavelengths (821) in the middle area, while column (813) is generally aligned with a small band of wavelengths (823) neighboring band (821). Other bands would be aligned with other columns in a similar fashion. Should the band of wavelengths (821) in column (811) be desired for measuring, the mirrors in that column (811) will be offset from the other mirrors on the MMA (107) in their position. Specifically, the column (811) will generally be at position +X (corresponding, for example, to light channel (211)) when the remaining columns (including column (813)) are generally at position −X (corresponding, for example, to light channel (213)) and vice-versa.

As is readily apparent, a single column need not be segregated and any single column or combination of columns, up to and including all columns can be included in the segregation. Each of the segregated columns may then be used to interrogate the sample and be referenced as the MMA (107) mirrors shift between positions. As should also be recognized, the unselected columns can also additionally or alternatively be used to interrogate the sample as the two groups cycle between the two channels (211) and (213).

FIG. 11B provides for an alternative arrangement. In FIG. 11B the spectrum band (821) is arranged on a diagonal (815) with the MMA (107). This provides much of same functionality of FIG. 11A, but because of the orientation of each mirror relative the spectrum (with part of each band overlapping neighboring bands) an additional form of optical smoothing can be achieved by segregating various diagonals instead of columns.

The ability of the MMA (107) to provide for any number of wavelength bands, as selected, being used for the evaluation can allow the spectroscope (100) to perform a large number of dynamic adjustments on the resultant signals received from the sample. Because the wavelength bands (821) can be individually segregated and therefore acted upon, a user can select the nature of their interrogation of the sample in a wavelength dependent fashion.

Figure 12:
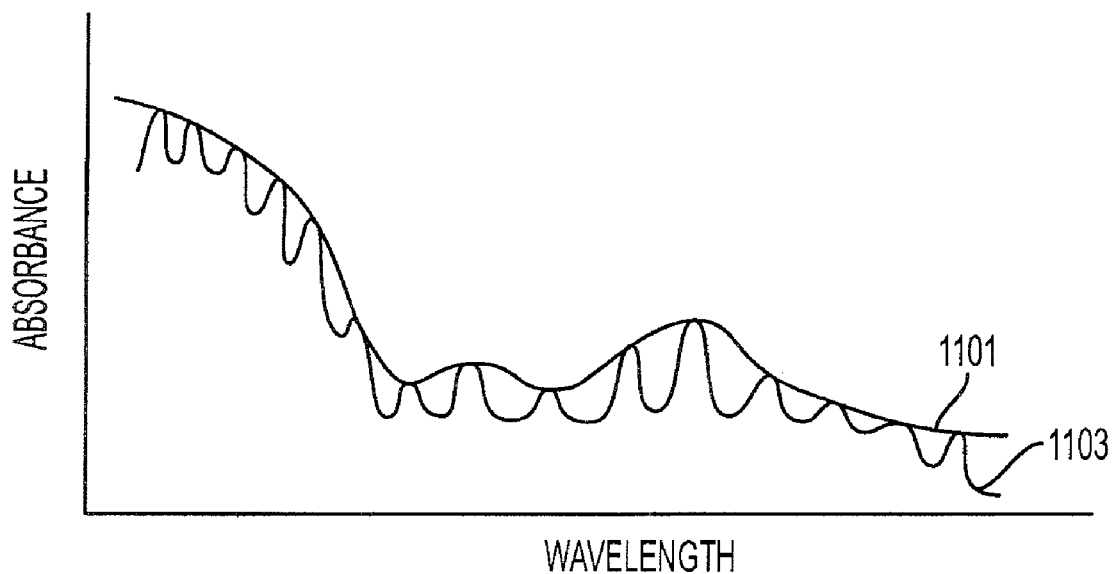
FIG. 12 provides for a graph showing how the spectroscope can be used for dynamic resolution control.

For example, FIG. 12 provides for a hypothetical graph showing the MMA (107) being used to allow for dynamic resolution control. The line (1101) is a much smoother curve and can be generated by having a large number of columns (811) be selected to interrogate simultaneously. On the other hand, line (1103) can be generated by having each individual column be used to interrogate separately. In this latter situation, the determination is much more exact as to absorbance of a smaller wavelength band, but the evaluation will generally take more time. Depending on the type of data output desired, one can select the mode of operation at the time of use.

Figure 13:
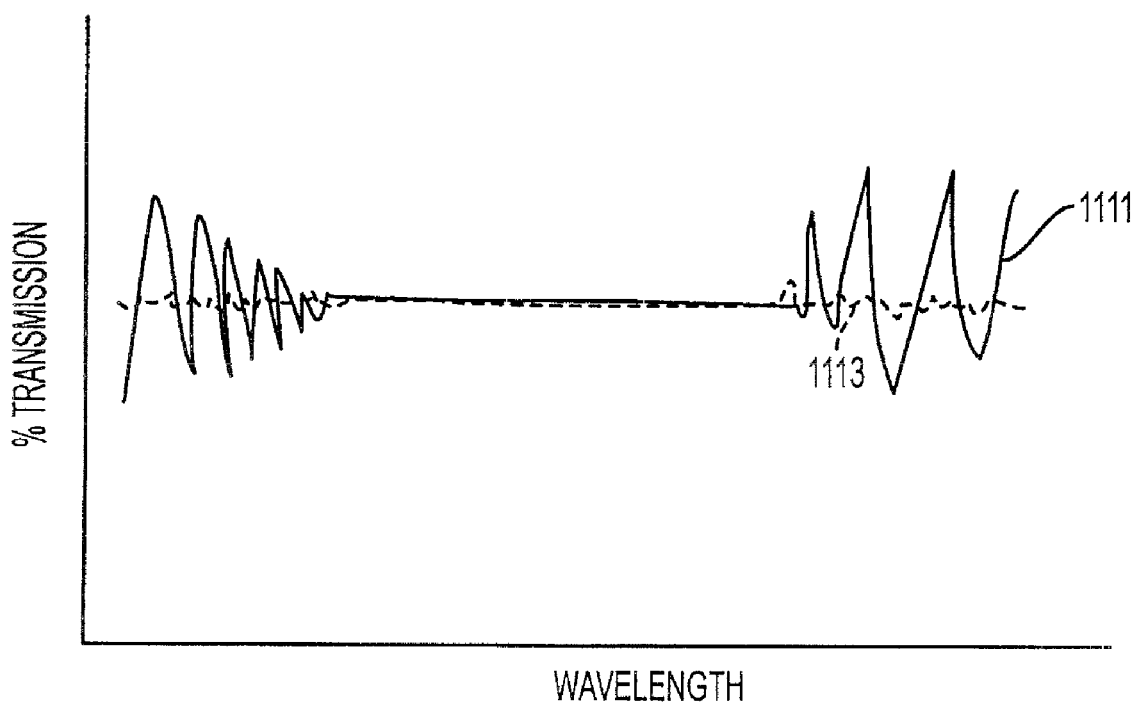
FIG. 13 provides a graph of how the spectroscope can be used to improve dynamic signal to noise ratio.

FIG. 13 provides for another such wavelength dependent structuring of the interrogation. In this hypothetical, the MMA (107) is used to dynamically improve signal to noise. Line (1111) is a noisy signal at both ends representing the normal occurrence with broad band light sources. The dashed line (1113), illustrates how the MMA can provide uniform intensity across the entire wavelength range through dynamic adjustment of the integration period, number of columns passing light, the number of rows in the column, or a plurality of other control schemes. in the most common implementation this allows the detector to integrate over a longer period of time which allows the end wavelengths to provide equivalent intensity compared to the center wavelength region effectively leveling out the percentage of transmission at all wavelengths. Alternatively, one skilled in the art would recognize that signal-to-noise can be equilibrated by controlling the mirrors' duty cycle, or by simply scaling the integration time for each band (821) so that the equivalent signal response results from each band being measured. In doing so, the reference channel could also be measured in a comparable fashion.

Figure 14A:
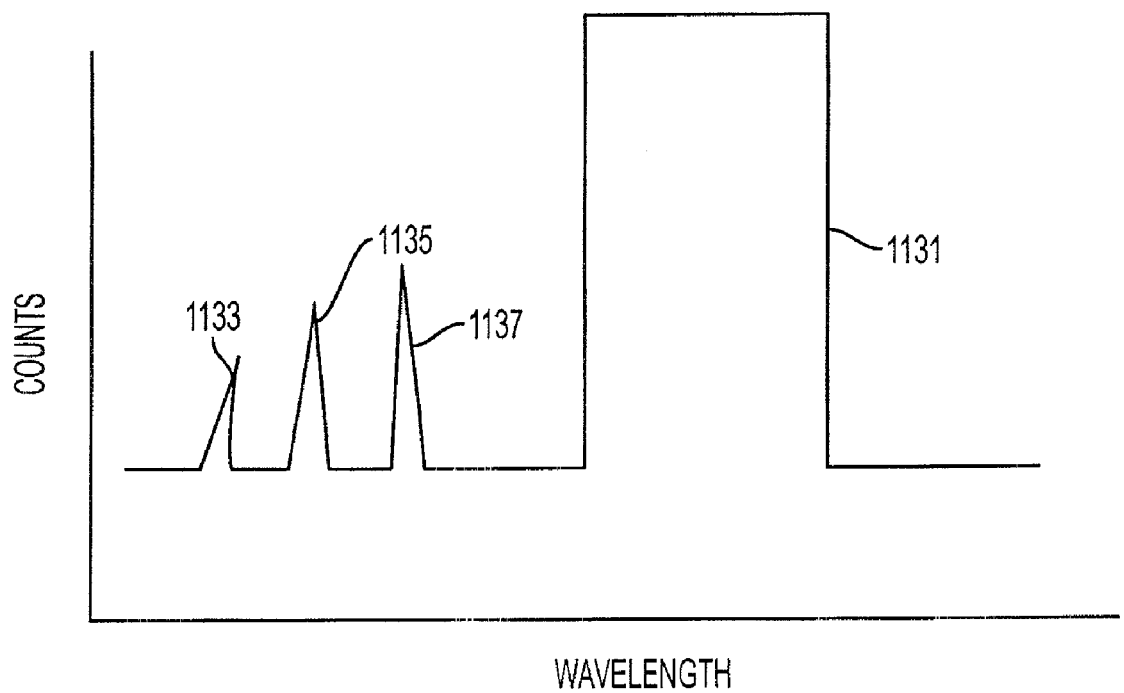
Figure 14B:
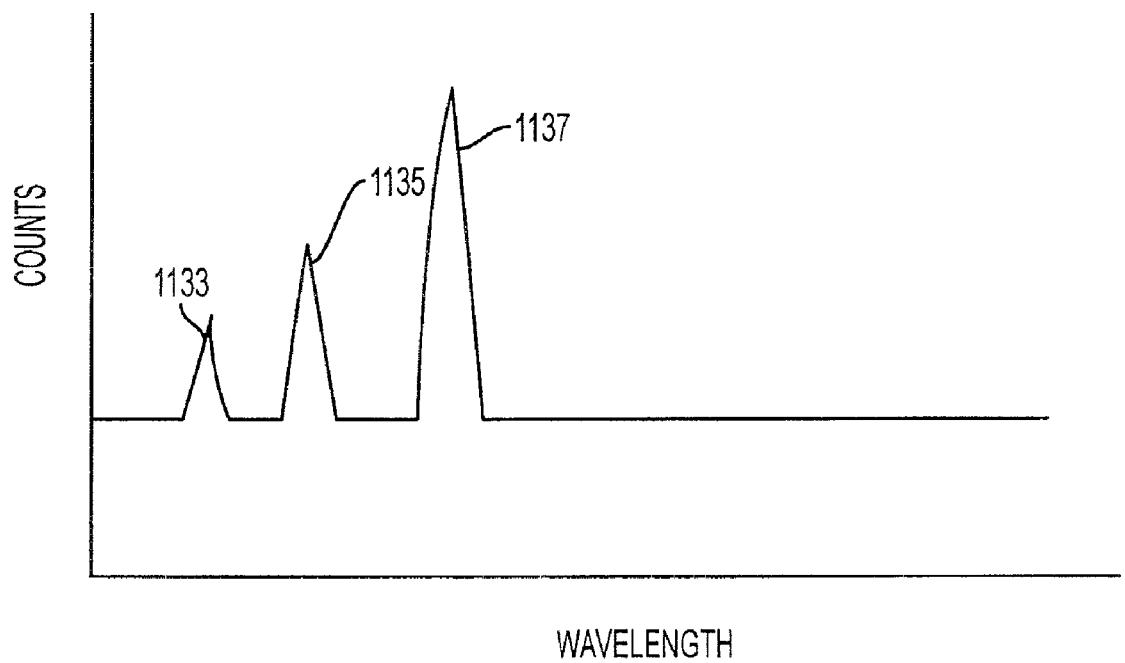
FIG. 14B shows the same graph after filtering.

FIG. 14 provides a representation of dynamic filtering. In FIG. 14A, there is provided a particular wavelength band (1131) of light which represents a saturated signal response. With certain configurations, such a saturated signal response may obscure or bias the details of the smaller signal responses (1133), (1135), and (1137). In FIG. 14B, the sections of the spectrum corresponding to the problematic wavelengths have been cut out, eliminating any transmission at that wavelength and allowing the smaller peaks (1133), (1135), and (1137) to be relatively more prominent.

Figure 15:
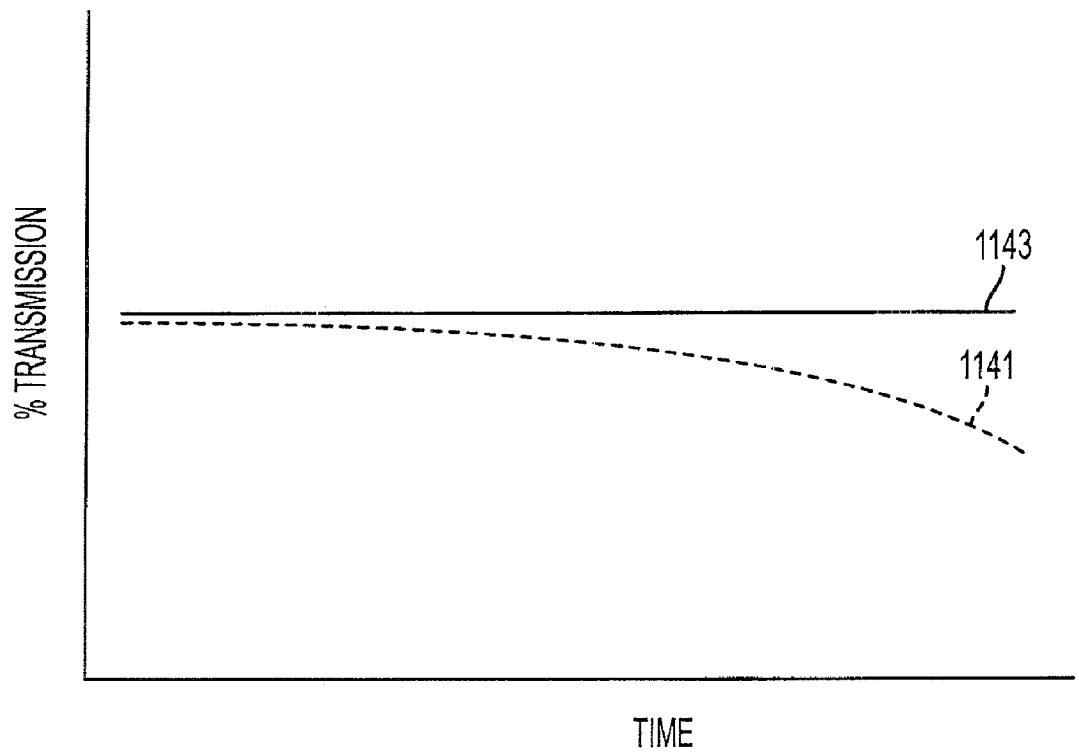
FIG. 15 provides a graph of how the spectroscope can be used for dynamic scaling.

FIG. 15 provides for adjustment of the sample channel by dynamic scaling or normalization over time. It is known that over time the operation of a spectroscope will change, causing the measured spectrum to change due to parts heating up or wearing out. This is particularly true of light sources. This is indicated by line (1141) showing how over time the transmission of a given wavelength has drifted. Effectively, this causes the spectroscope to loose its calibration. Because such changes can be detected by the reference channel (211) as not being due to the sample, the dynamic reference capability of the spectroscope (100) can be utilized to correct for the loss in calibration thereby allowing the actual percent transmission to approach the ideal (1143).

FIGS. 12 through 15 have provided for a number of different benefits from the ability to dynamically reference by providing two optical paths (211) and (213). In particular, the spectroscope (100) can provide for wavelength dependent structuring of the spectrum which is used to interrogate the sample. This structuring may be spatial structuring where particular elements of the light are controlled based on their spatial positioning, or may be temporal structuring where the light is modulated over time.

In operation, any mirror arranged at the preselected +X° state will direct incident wavelengths toward the sample detector (203) while mirrors at the −X° state will direct incident wavelengths toward the reference detector (201) or vice-versa, depending on specific arrangement. Further, when the mirrors are between states, the light may be directed into a light trap (111) as shown in FIG. 2A.

It should be apparent that with a generally single wavelength, or small wavelength band, incident on each of the mirrors in the MMA (107), one can adjust the mirrors to supply those wavelength bands incident on the mirrors, to either detector (201) and (203) individually, or in any combination. The mid point (or 0°) state on most current MMA (107) devices is generally unstable and therefore light cannot be reliably directed using this state at this time. However, it can be recognized that if a third position of the mirror is sufficiently stable, which is believed to be soon obtainable with current technology, this position can be used to provide for a discrete third channel. In a preferred embodiment, this third channel would be for a dark signal measurement where there is no light incident on either the reference channel (211) or sample channel (213). As indicated in FIG. 2A, with the minors arranged at a third state (such as 0°) the wavelengths are directed into an optical trap (111), rendering both detectors (201) and (203) temporarily dark. This allows each detector (201) and (203) to take a "dark signal" measurement simultaneously saving processing steps. Additionally, even without the third position, all wavelengths can be directed to either detector (201) or (203) thereby removing all incident radiation from the other detector (201) or (203), which also enables near real-time dark signal measurement at the currently dark detector (201) or (203). This operation provides for additional calibration in determining "dark noise" (the thermal response of detectors (201) and (203) as well as any light incident on the detectors (201) and (203) which is not being purposefully directed to them by action of the MMA (107)), which can then be nulled by the spectroscope (100) control system.

Figures 16A, 16B:
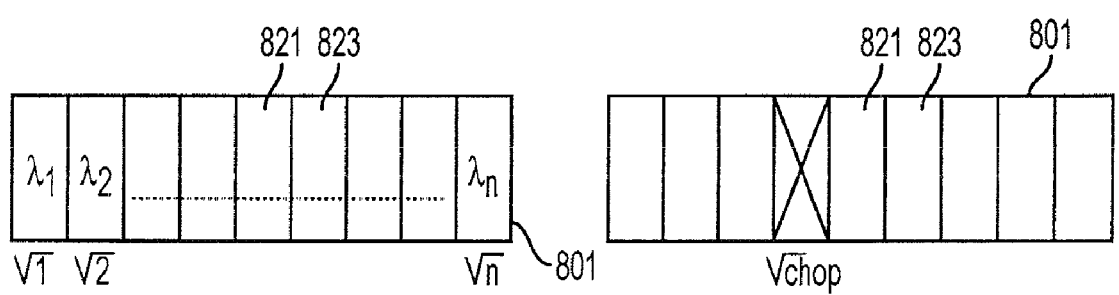
FIG. 16 provides for two indications of how wavelength segments of the spectrum can be modulated to provide for Fast Fourier Transform (FFT) analysis (FIG. 16A) and optical chopping (FIG. 16B).

It will also be understood that while FIGS. 8A and 8B shows the monitoring of a single band in a scanning mode. FIGS. 16A and 16B provide for a couple of examples of how spectrum columns (821) can be modified to perform some types of structuring. In FIG. 16A, each column has its bandwidth frequency modulated at independent frequencies so as to provide for Fast Fourier Transform (FFT) analysis. In an alternative approach shown in FIG. 16B instead of modulating each wavelength at a different frequency, each band can be modulated at the same frequency sequentially to provide signal-to-noise improvement via optical chopping. The spectroscope (100) can also be used to measure multiple bands simultaneously using the MMA (107) to temporally process the incident radiation simply by altering the frequency that each individual wavelength band is modulated. This in turn imparts a temporal structure to the incident radiation. This methodology enables the spectroscope (100) to read all wavelengths simultaneously, or multiplexed, as opposed to individually scanning each individual wavelength or wavelength band at either detector (201) or (203). This is simply an alternative method for spectral processing utilizing the same spectroscope (100). While the embodiment shown in FIG. 2A uses the MMA (107) for spectral filtering, an alternative embodiment may use the MMA (107) for spatial, spectral, or temporal filtering, thus enabling an alternative means of data processing, such as Hadamard Transform Spectroscopy or Fourier Transform Spectroscopy respectively.

The use of an MMA for Hadamard Transform Spectroscopy and Fourier Transform spectroscopy has been documented by DeVerse et al. in "Realization of the Hadamard Multiplex Advantage Using a Programmable Optical Mask in a Dispersive Flat-Field Near-Infrared Spectrometer." *Applied Spectroscopy*, vol. 54 No. 12, pgs. 1751-1758 (2000), the entire disclosure of which is herein incorporated by reference. However, in DeVerse, implementations were limited due to the fact that only a single optical channel was utilized. Operating the spectroscope (100) as a Hadamard or Fourier Transform spectral analyzer and utilizing the dual channel nature of spectroscope (100), and algorithms known to those versed in the art of signal processing to deconvolute the reference and sample channels spectral content, the spectroscope (100) is able to dynamically calibrate itself and/or scale output using implementations similar to those of DeVerse.

Further, it should be recognized that the spectroscope (100) is generally not limited by hardware configuration to any particular analysis technique but may be used for a variety of spectroscopy techniques including, but not limited to, those described in Spudich et al. "Potential for Using a Digital Micromirror Device as a Signal Multiplexer in Visible Spectroscopy." *Applied Spectroscopy*, vol. 57 No. 7, pgs. 733-736 (2003); U.S. Pat. No. 6,781,691; and U.S. Patent Publications US 2004/0239923 and US 2004/0169858, The entire disclosure of all of these documents is herein incorporated by reference.

Generally, as should be apparent from the figures, the spectroscope (100), utilizing the MMA (107), allows for the control system to select any wavelength band or bands for sampling, and to temporally structure bands, without requiring hardware reconfiguration. Instead, the component wavelength band(s) desired is simply selected by the control system based on what is available in the incident light, and how it instructs the MMA (107) operation. After that, the selected band(s) being used for sampling can be referenced against a reference signal with relative ease simply by redirecting the band(s) to the reference path. The measurement of a sample therefore shows good accuracy and stability for a spectroscope (100) having a high number of useable and alterable spectrums without need of hardware reconfiguration.

Figure 17:
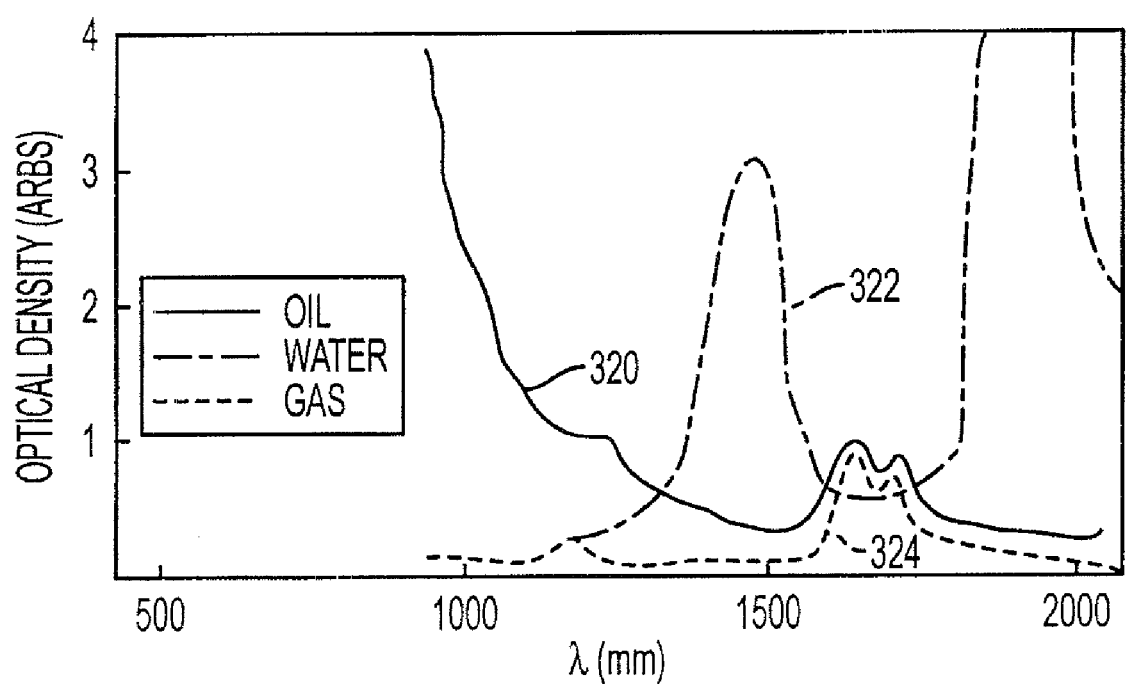
FIG. 17 illustrates a sample spectrum measured with an embodiment of the spectroscope illustrating oil, water, and gas constituents in the fluid.

In operation, the spectroscope (100) in use in a fluid processing system tool (10) may evaluate formation fluid while within a hydrocarbon well. Oil, water, and gas are major constituents of fluids produced in hydrocarbon wells although other materials may also be present. FIG. 17 is a plot of optical density in arbitrary units (ordinate) versus wavelength $\lambda$ in nanometers (nm) (abscissa) for oil, water and gas. Curves (320), (322) and (326) represent oil, water and gas, respectively. It is apparent that each constituent exhibits at least one significant diversion or "peak." As an example, water exhibits two large peaks at approximately 1450±50 nm and 1940±50 nm. Methane exhibits a strong peak in the range of about 1600 nm to 1650 nm. Hydrocarbon is associated with the peak structure in the range of 1650 nm to 1780 nm. Additionally, both carbon dioxide ($CO_2$) and hydrogen sulfide ($H_2S$) are measurable in the near infra-red region under specific concentration conditions. Heavy crude oil exhibits a large continuum below approximately 1100 nm whereas light curdes have a measurable absorbance response in the visible spectral region. It is apparent that oil, water and gas exhibit unique spectral characteristics. A measure of a spectrum of the type illustrated in FIG. 17 can, therefore, be used to identify constituents of fluid and the device of FIG. 2A may be used to measure such a spectrum by sampling fluids present downhole. Furthermore, the magnitude of components of a measured composite spectrum can be used to obtain concentrations of constituents. In addition, the measured spectrum can be used to obtain other physical or chemical properties.

In view of the above discussion of the operation of the spectroscope (100), it is apparent that the MMA (107) can be configured so that light of one or more predetermined wavelengths impinges upon the fluid (180). This renders the spectroscopic measurement sensitive to one or more constituents of the fluid. As an example, if the spectroscope (100) is configured to emit light at $\lambda$=1450±50 nm and 1940±50 nm bands in the sample channel, the spectroscopic response of the sample channel will be most sensitive to the water constituent in the fluid (180). As another example, the spectroscope (100) can be configured so that the sample channel "sweeps" wavelengths over a predetermined range of energy bands. As an example, the spectroscope (100) can be configured to emit sample light in contiguous energy bands of 10 nm in width, and ranging from 1000 to 2100 nm, The spectroscopic response of the spectroscope (100) will yield a spectrum, with components representing oil gas and water constituents, of the form shown in FIG. 17. The measured spectrum can then be used to determine relative concentrations of the fluid constituents using a variety of spectral analyses methodologies. In addition, the measured spectrum can be used to obtain other physical or chemical properties.

Processing of the measured data can be performed in the downhole processor disposed preferably in the spectroscope tool section (16) of the tool (10), in the surface processor disposed in the surface equipment (32), or in both processors. Downhole or surface processing of the data may be governed by the configuration of the formation tester system and the telemetry bandwidth available. Alternately, tool response data can be stored in memory within or operatively connected to the tool (10) for retrieval at the surface. Results may be tabulated as a function of time and/or depth at which they are measured, and output by the surface equipment (32) using any desired reporting format including, but not limited to a "log" or a "strip chart".

Embodied as a wellbore fluid analysis system (5), the tool (10) is typically disposed at a predetermined depth within the wellbore (28) in which fluid is flowing, either from an over pressured producing formation or from the action of a well pump. The probe section (12) comprises an input port through which fluid flows into the tool (10). As in the production logging tool embodiment, the pump tool section (20) and the sample tool section (18) (see FIG. 1) are not required. Fluid flow through the tool (10), and measurements made with the tool (10), are both essentially the same as described in the production logging embodiment. The tool (10) measures fluid properties as a function of time and/or depth. Fluid monitoring time can span days or even weeks. Once again, the typical parameters of interest are related to the oil, water and gas constituents and the chemical and physical properties of the flowing fluid.

As mentioned previously, the spectroscope (100) can be embodied in a production logging system. Referring to FIG. 1, the pump tool section (20) and the sample tool section (18) are not required in an embodiment designed for production logging. In a production logging embodiment, the tool (10) is conveyed along the wellbore (28). The probe section (12) comprises a port into which wellbore fluid flows due to the relative motion of the conveyed tool (10) or the produced fluid. Fluid may flow through the auxiliary section (14), wherein measurements related to fluid constituent phase flow rates, composite fluid density, phase holdup factors and any other desired parameter can be made. Fluid may then flow through the spectroscope tool section (16). Measurements related to the constituents, chemical and/or physical properties of the fluid are made in the spectroscope tool section (16), as described in previous sections of this disclosure. After flowing through the spectroscope tool section (16), the fluid exits the tool (10) through an exit port (not shown) and returns to the wellbore (28). Spectroscopic measurements are combined with measurements from the auxiliary section, in the processor (not shown) preferably in the spectroscope tool section (16), to obtain production logging parameters of interest such as volume flow rates for oil, water and gas. These parameters of interest are made as a function of time and/or depth (40) in the wellbore (28) thereby generating a production log.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A tool for measuring properties of a fluid downhole, the tool comprising:
    a port for obtaining a sample of fluid downhole; and
    a spectroscope, the spectroscope including:
        a sample channel that evaluates said fluid;
        a reference channel; and
        an adaptive optical element which comprises elements that are sequentially oriented to direct light, at sample wavelength, into the sample channel and into the reference channel;
        wherein response of the sample channel and response of the reference channel are combined to yield a measure of a property of said fluid and to correct the measure for systematic changes in the spectroscope.

2. The tool of claim 1 wherein said spectroscope evaluates at least one chemical or physical property of said fluid within said wellbore.

3. The tool of claim 1 wherein said tool is part of a wireline formation tester system.

4. The tool of claim 1 wherein said tool is part of a production logging system.

5. The tool of claim 1 wherein said tool is part of downhole fluid analysis system.

6. The tool of claim 1 wherein said tool is part of a Logging While Drilling/Measurement While Drilling (LWD/MWD) formation tester system.

7. The tool of claim 1 wherein said spectroscope further comprises means for determining spectroscope dark Current.

8. The tool of claim 7 further comprising:
    A control system which orients elements of the adaptive optical element such that the light is directed away from either the sample channel or the reference channel, and responses of the reference detector and sample detector, respectively, are used to determine the respective channel dark currents.

9. A system for measuring properties of a fluid from within a wellbore, the system comprising:
    a tool, the tool including;
        a wellbore isolation element for isolating a portion of an earth formation;
        a port for obtaining a sample of formation fluid from said isolated portion; and
        a spectroscope, said spectroscope including:
            a light source;
            an adaptive optical element which is used for wavelength filtering;
            a sample channel comprising a sampling accessory in optical contact with the fluid;
            a sample detector; and
            a reference channel comprising a reference detector;
        a control system that orients elements of said adaptive optical element such that light at a sample wavelength is directed into said sample channel, and alternately orients elements of said adaptive optical element such that the light at said sample wavelength is directed into said reference channel; and
        a processor for combining responses of said sample detector and said reference detector to obtain a measure of at least one property of a fluid within a wellbore and to correct the measure for systematic changes in said spectroscope.

10. The system of claim 9 wherein said spectroscope further comprises means for determining spectroscope dark current.

11. The system of claim 10 wherein said control system orients elements of the adaptive optical element such that the light is directed away from either the sample channel or the reference channel, and responses of the reference detector and sample detector, respectively, are used to determine the respective channel dark currents.

12. The system of claim 11 wherein these measurements are used subsequently to correct spectroscope measurements for the adverse effects of background drift.

13. The system of claim 9 wherein said tool further includes:
   a spectroscope tool section in which said spectroscope is disposed; and
   a probe section in which said part is disposed.

14. The system of claim 13 wherein said tool further includes:
   a pump tool section.

15. The system of claim 9 further comprising:
   a surface telemetry unit;
   an electronics and telemetry tool section disposed in the tool including a downhole telemetry unit; and
   a data conduit operationally connecting said downhole telemetry unit with the surface telemetry unit thereby allowing said measure of said at least one property to be sent by telemetry to said surface telemetry unit.

16. The system of claim 9 further comprising a sampling section for retaining a sample of said formation fluid.

17. The system of claim 9 wherein said tool is part of a wireline formation tester system.

18. The system of claim 9 wherein said tool is part of a Logging While Drilling/Measurement While Drilling (LWD/MWD) formation tester system.

19. A method for measuring a property of a fluid within a wellbore, the method comprising:
   disposing a spectroscope within the wellbore, the spectroscope comprising a sample channel that interacts with a fluid, a reference channel, and an adaptive optical element;
   sequentially orienting said adaptive optical element to direct light, at a sample wavelength, into said sample channel and into said reference channel; and
   combining a response of said sample channel and a response of said reference chamber to obtain a measure of a property of the fluid and to correct the measure for systematic changes in the spectroscope.

20. The method of claim 19 wherein said method is performed by a wireline formation tester system.

21. The method of claim 19 wherein said method is performed by a production logging system.

22. The method of claim 19 wherein said method is performed by a downhole fluid analysis system.

23. The method of claim 19 wherein said method is performed by a Logging While Drilling/Measurement While Drilling (LWD/MWD) formation tester system.

24. The method of claim 19 wherein said spectroscope further comprises means for determining spectroscope dark current.

* * * * *